(12) United States Patent
Hyde et al.

(10) Patent No.: US 8,401,633 B2
(45) Date of Patent: Mar. 19, 2013

(54) SUBDERMAL MATERIAL DELIVERY DEVICE

(75) Inventors: Roderick A. Hyde, Redmond, WA (US); Jordin T. Kare, Seattle, WA (US); Dennis J. Rivet, Portsmouth, VA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

(21) Appl. No.: 12/080,809

(22) Filed: Apr. 3, 2008

(65) Prior Publication Data

US 2009/0240241 A1 Sep. 24, 2009

Related U.S. Application Data

(63) Continuation of application No. 12/077,938, filed on Mar. 20, 2008.

(51) Int. Cl.
*A61N 1/30* (2006.01)

(52) U.S. Cl. .......................... 604/20; 604/891.1

(58) Field of Classification Search . 604/288.01–288.04
See application file for complete search history.

(56) References Cited

U.S. PATENT DOCUMENTS

| | | | |
|---|---|---|---|
| 4,784,645 A * | 11/1988 | Fischell | 604/153 |
| 4,784,646 A * | 11/1988 | Feingold | 604/175 |
| 5,352,192 A | 10/1994 | Byrne et al. | |
| 5,551,953 A | 9/1996 | Lattin et al. | |
| 6,283,949 B1 * | 9/2001 | Roorda | 604/288.02 |
| 6,287,293 B1 * | 9/2001 | Jones et al. | 604/891.1 |
| 6,322,532 B1 | 11/2001 | D'Sa et al. | |
| 7,090,668 B1 | 8/2006 | U et al. | |
| 7,108,686 B2 * | 9/2006 | Burke et al. | 604/891.1 |
| 2002/0156462 A1 * | 10/2002 | Stultz | 604/891.1 |
| 2003/0195523 A1 | 10/2003 | Futsz | |
| 2003/0233067 A1 | 12/2003 | McIntosh et al. | |
| 2004/0077991 A1 | 4/2004 | Kumar et al. | |
| 2004/0260234 A1 * | 12/2004 | Srinivasan et al. | 604/66 |
| 2004/0267231 A1 | 12/2004 | Sun et al. | |
| 2005/0038415 A1 | 2/2005 | Rohr et al. | |
| 2005/0136092 A1 * | 6/2005 | Rotem et al. | 424/423 |
| 2005/0137537 A1 | 6/2005 | Watson et al. | |
| 2005/0143686 A1 | 6/2005 | Shevlin | |
| 2006/0178648 A1 * | 8/2006 | Barron et al. | 604/288.02 |
| 2007/0043320 A1 * | 2/2007 | Kenany | 604/68 |
| 2007/0233017 A1 | 10/2007 | Zinn et al. | |
| 2008/0051723 A1 | 2/2008 | Laermer et al. | |
| 2008/0208236 A1 | 8/2008 | Hobbs et al. | |
| 2009/0258062 A1 | 10/2009 | Horstmann et al. | |

* cited by examiner

*Primary Examiner* — Kevin C Sirmons
*Assistant Examiner* — Brandy C Scott
(74) *Attorney, Agent, or Firm* — Suiter Swantz pc llo

(57) ABSTRACT

A method may include placing a first device on a first side of a skin portion of a subject and transferring a material through the skin portion of the subject from the first device to a subdermal second device disposed on a second side of the skin portion of the subject.

17 Claims, 18 Drawing Sheets

SUBDERMAL MATERIAL DELIVERY DEVICE

CROSS-REFERENCE TO RELATED APPLICATIONS

The present application is related to and claims the benefit of earliest available effective filing date(s) from the following listed application(s) (the "Related Applications") (e.g., claims earliest available priority dates for other than provisional patent applications; claims benefits under 35 USC §119(e) for provisional patent applications), and incorporates by reference in its entirety all subject matter of the following listed application(s); the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith:
1. For purposes of the USPTO extra-statutory requirements, the present application constitutes a continuation of United States Patent Application entitled SUBDERMAL MATERIAL DELIVERY DEVICE, naming Roderick A. Hyde; Jordin T. Kare; Dennis J. Rivet; and Lowell L. Wood Jr as inventors, filed 20 Mar. 2008, application Ser. No. 12/077, 938, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation of its parent applications as set forth above, but expressly points out that such designations are not to be construed in any way as any type of commentary and/or admission as to whether or not the present application contains any new matter in addition to the matter of its parent application(s).

BACKGROUND

Subcutaneous devices can be utilized to dispense material (such as medicine) to subjects in which such devices have been implanted. These devices may be desirable for ensuring patient compliance and convenience. However, reloading such devices may require invasive techniques for refilling the dispensed material, including repeatedly puncturing the skin of the subject or placing a port in the subject's skin.

SUMMARY

In one aspect, a method includes but is not limited to placing a first device on a first side of a skin portion of a subject and transferring a material through the skin portion of the subject from the first device to a subdermal second device disposed on a second side of the skin portion of the subject. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein-referenced method aspects depending upon the design choices of the system designer.

In one aspect, a system includes but is not limited to a means for placing a first device on a first side of a skin portion of a subject and a means for transferring a material through the skin portion of the subject from the first device to a subdermal second device disposed on a second side of the skin portion of the subject. In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure.

A device includes a reservoir configured for placement subdermally to a skin portion of a subject and an input port operably connected to the reservoir for receiving a material transferred through the skin portion of the subject from a second device placed on a second side of the skin portion of the subject.

A device includes a reservoir configured for placement externally to a skin portion of a subject and an output port operably connected to the reservoir for transferring a material through the skin portion of the subject to a second device placed on a second side of the skin portion of the subject.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

The use of the same symbols in different drawings typically indicates similar or identical items.

DETAILED DESCRIPTION

Figure 1:
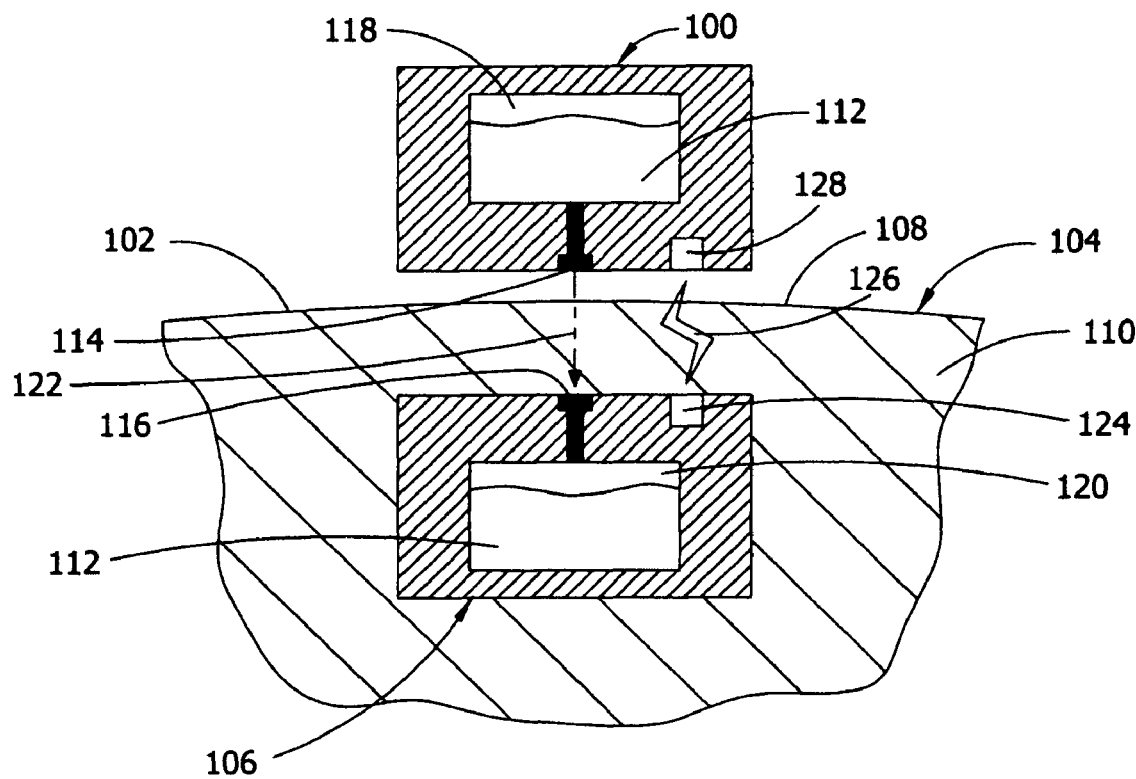
FIG. 1 is a schematic of a device for transferring material through a skin portion of a subject to a second subcutaneous device.

In the following detailed description, reference is made to the accompanying drawings, which form a part hereof. In the drawings, similar symbols typically identify similar components, unless context dictates otherwise. The illustrative embodiments described in the detailed description and drawings, and claims are not meant to be limiting. Other embodiments may be utilized, and other changes may be made, without departing from the spirit or scope of the subject matter presented here.

Referring generally to FIGS. 1 through 6, a first device 100 for transferring material through a skin portion 102 of a subject 104 to a subcutaneous/subdermal second device 106 is described in accordance with embodiments. The subject 104 may generally be defined as any biological entity having a protective skin covering, such as a mammalian entity (e.g., a human, a dog, a cat, or another mammal), an avian entity (e.g., a bird of prey), as well as other biological entities having protective skin coverings. The first device 100 is placed on a first side 108 of the skin portion 102 of the subject 104 (e.g., externally to the skin portion 102 of the subject 104), and the subdermal second device 106 is placed on a second side 110 of the skin portion 102 of the subject 104 (e.g., subdermally to the skin portion 102 of the subject 104). Then a material 112 may be transferred from the first device 100 to the subdermal second device 106 through the skin portion 102 of the subject 104.

In some embodiments, the subdermal second device 106 may be utilized for performing a bioassay/analytical procedure on the subject 104. For example, in one embodiment, an assay is performed utilizing a material 112 that reacts to the subject's blood. The material 112 may be replenished during the course of the assay by transferring additional material 112 through the skin portion 102 of the subject 104 from the first device 100 to the subdermal second device 106. It will be appreciated that while the material 112 has been described with some specificity as material selected for performing a bioassay/analytical procedure, a wide variety of materials may be utilized with the first device 100 or the subdermal second device 106, including materials selected for diagnosing, treating, preventing, or alleviating symptoms of an illness/disease. Further, it is contemplated that materials selected for establishing or maintaining an overall level of health/wellness for the subject 104 may be utilized as well, including vitamins, minerals, nutrients, and the like. In some embodiments, the first device 100 is configured for the transdermal transfer of material through the skin portion 102 of the subject 104 in a needle-free manner, i.e., without extending any portion of the first device 100 through the skin portion 102 of the subject 104 and without connecting the first device 100 to any mechanical instrument extending through the skin portion 102 of the subject 104.

In an embodiment, the material 112 is transferred utilizing iontophoresis (i.e., active transport within an electric field). For example, a first electrical polarity may be established for the first device 100 in opposition to a second electrical polarity for the skin portion 102 of the subject 104 or for the subdermal second device 106. Then, the material 112 may be transferred through the skin portion 102 of the subject 104 to the subdermal second device 106 utilizing iontophoresis. For instance, in an embodiment, the first electrical polarity for the first device 100 is set in opposition to a second electrical polarity for the subdermal second device 106, creating an electric field between the first device 100 and the subdermal second device 106. The material 112, which may have a charge corresponding to the first electrical polarity of the first device 100, is then transported from the first device 100 through the skin portion 102 of the subject 104 to the subdermal second device 106 via repulsive electromotive force. It will be appreciated that the polarities of one or both of the first device 100 and the subdermal second device 106 may be controlled as needed to assist with the transfer of the material 112.

In another embodiment, the material 112 is transferred utilizing one or more jets for propelling the material 112. For example, the first device 100 may include an output port 114 with a microjet for propelling the material 112 through the skin portion 102 of the subject 104 to an input port/receiving port 116 of the subdermal second device 106. A microjet utilizes pressure to force or displace material through an extremely small diameter opening, i.e., a micro-nozzle (for example, approximately 50-200 μm), enabling the material to penetrate at least one dermal layer of the subject 104 without substantially damaging the dermal layer. For example, the first device 100 may utilize pressure to force or displace the material 112 through a micro-nozzle, enabling the material 112 to penetrate at least one dermal layer of the subject 104 without substantially damaging the dermal layer. In this example, the micro-nozzle may be approximately cylindrical in shape and have a diameter of approximately 50-150 μm. By way of another example, the output port 114 may comprise a MEMS (microelectromechanical systems) based microjet formed by a piezoelectric transducer bonded to a silicon wafer with a micro-nozzle which forces or displaces the material 112 through the micro-nozzle enabling the material 112 to penetrate at least one dermal layer of the subject 104 without substantially damaging the dermal layer.

The output port 114 may comprise a liquid microjet that utilizes pressure to force or displace a small volume of liquid through a micro-nozzle enabling the liquid to penetrate at least one dermal layer of the subject 104 without substantially damaging the dermal layer. For example, the first device 100 may utilize pressure to force or displace a liquid material 112 through a micro-nozzle enabling the material 112 to penetrate at least one dermal layer of the subject 104 without substantially damaging the dermal layer. In this example, the micro-nozzle may be cylindrical in shape and have a diameter of approximately 50-100 µm. By way of another example, the first device 100 may comprise a MEMS-based liquid microjet formed by a piezoelectric transducer bonded to a silicon wafer with a micro-nozzle which forces or displaces the material 112 as a liquid through the micro-nozzle enabling the material 112 to penetrate at least one dermal layer of the subject 104 without substantially damaging the dermal layer.

The output port 114 may comprise a pulsed liquid microjet that utilizes pressure to force one or more pulses of a liquid material 112 through a nozzle enabling the pulse of liquid to penetrate at least one dermal layer of the subject 104 without substantially damaging the dermal layer. For example, the first device 100 may utilize pulses of pressure to force or displace liquid through a micro-nozzle at a frequency of approximately 1 Hz to 10 Hz enabling the material to penetrate at least one dermal layer of the subject 104 without substantially damaging the dermal layer. By way of another example, the first device 100 may comprise a MEMS-based liquid microjet formed by a piezoelectric transducer bonded to a silicon wafer with a micro-nozzle which utilizes pulses of pressure at a frequency of approximately 1 Hz to 10 Hz to force or displace the material 112 as a liquid through the micro-nozzle enabling the material 112 to penetrate at least one dermal layer of the subject 104 without substantially damaging the dermal layer.

A microjet may include a liquid jet having a jet diameter in the range of micrometers or smaller. A microjet may include a liquid jet having a supersonic speed, or alternatively, a subsonic speed. In further embodiments, the material 112 may be transported through the skin portion 102 of the subject 104 to the receiving port 116 of the subdermal second device 106 in an ultra fine stream. An ultra fine stream may include a liquid stream having a diameter in the range of nanometers or larger. In still further embodiments, the material 112 may be transported through the skin portion 102 of the subject 104 to the receiving port 116 of the subdermal second device 106 in a pulsed stream.

In other embodiments, the first device 100 may force may force the material 112 through at least one dermal layer of the subject 104 utilizing high pressure. High pressure may allow a very thin stream to puncture an isolated portion of the at least one dermal layer of the subject 104 rather than transferring the impact to a larger area of the at least one dermal layer and thus not substantially damage the at least one dermal layer. High pressure may be pressure sufficient to force the material 112 through at least one dermal layer of the subject 104 without substantial damage to the at least one dermal layer of the subject 104. For example, the first device 100 may force the material 112 through at least one dermal layer of the subject 104 at a velocity of at least approximately 100 m/s. The first device 100 may include a pressure generating mechanism for generating pressure including, but not limited to, a spring-loaded pressure generating mechanism or a piezoelectric pressure generating mechanism. For example, the first device 100 may comprise an electrically powered piezoelectric actuator which displaces a plunger in an acrylic micro-nozzle to force the material 112 through at least one dermal layer of the subject 104. In this example, the volume and velocity of the material 112 may be controlled by controlling the voltage and rise time of the electrically powered piezoelectric actuator. By way of another example, the first device 100 may comprise a loaded spring which displaces a plunger in a micro-nozzle to force the material 112 through at least one dermal layer of the subject 104. By way of still another example, the first device 100 may comprise a MEMS-based microjet formed by a piezoelectric transducer bonded to a silicon wafer with a micro-nozzle approximately 5-10 µm in diameter where a continuous pressure wave generated by the piezoelectric transducer propagates the material 112 toward the micro-nozzle to force the material 112 through at least one dermal layer of the subject 104.

In an embodiment, at least one dermal layer of the subject 104 may be subjected to an energy field to aid in forcing the material 112 through the at least one dermal layer of the subject 104. Subjecting the at least one dermal layer of the subject 104 to the energy field may create one or more pores in the at least one dermal layer or may increase the permeability of the at least one dermal layer, aiding in forcing the material 112 through the at least one dermal layer. The energy field may include, but is not limited to, an electrical energy field or an ultrasonic energy field. The first device 100 or the subdermal second device 106 may subject the at least one dermal layer 102 to the energy field.

It will be appreciated, in light of the description provided herein, that a number of techniques may be utilized for transporting the material 112 from the first device 100 to the subdermal second device 106 through the skin portion 102 of the subject 104. Further, more than one microjet, ultra fine stream, or pulsed stream may be utilized simultaneously over an area of the skin portion 102 of the subject 104.

In certain embodiments, transfer of the material 112 from the first device 100 to the subdermal second device 106 may be assisted by sonophoresis, in which the skin portion 102 of the subject 104 becomes temporarily more permeable for increasing the absorption of topically applied compounds. For example, ultrasonic waves may be utilized to stimulate micro-vibrations within the skin portion 102 of the subject 104, increasing the ability of the material 112 to migrate through the skin portion 102 to the subdermal second device 106. In an embodiment, the material 112 is topically applied to the first side 108 of the skin portion 102 of the subject 104 (e.g., via the output port 114 of the first device 100). The first device 100 or the subdermal second device 106 may then generate ultrasonic waves, assisting in the migration of the material 112 through the skin portion 102 of the subject 104 from the first side 108 of the skin portion 102 to the second side 110 of the skin portion 102, and then to the receiving port 116 of the subdermal second device 106.

The first device 100 may include a first reservoir 118 for storing the material 112. Further, the subdermal second device 106 may include a second reservoir 120 for storing the material 112. In an embodiment, the first reservoir 118 of the first device 100 is at least partially deloaded to transfer the material 112 through the skin portion 102 of the subject 104 to the subdermal second device 106. The material 112 may then be collected by the subdermal second device 106 in the second reservoir 120. In order to ensure that the material 112 reaches the subdermal second device 106, the second reservoir 120 of the subdermal second device 106 may be aligned with the first reservoir 118 of the first device 100. In an embodiment, this may be accomplished by at least substantially aligning the output port 114 of the first device 100 with the receiving port 116 of the subdermal second device 106.

Figure 5:
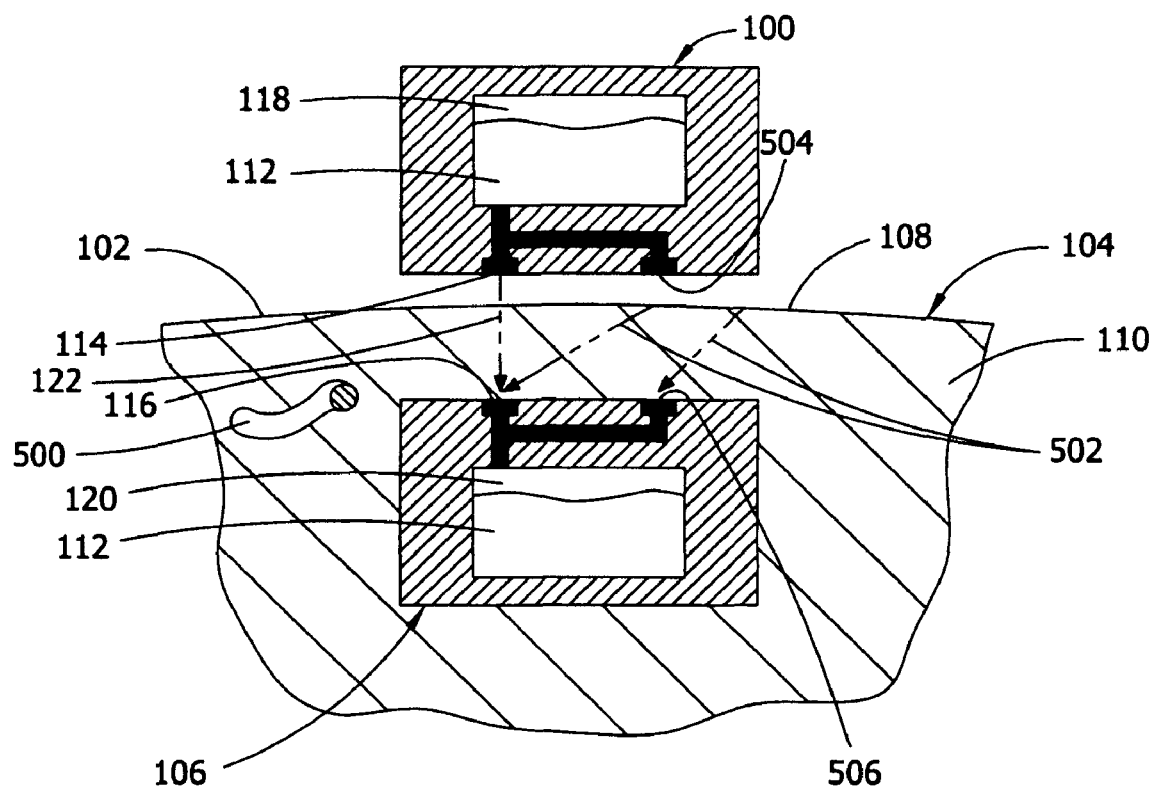
FIG. 5 is a still further schematic of a device for transferring material through a skin portion of a subject to a second subcutaneous device.

At least substantially aligning the output port 114 of the first device 100 with the receiving port 116 of the subdermal second device 106 may include defining a transcutaneous path 122 extending through the skin portion 102 of the subject 104 from the first device 100 to the subdermal second device 106. The material 112 may then be transferred through the skin portion 102 of the subject 104 generally along the transcutaneous path 122. In certain embodiments, the transcutaneous path 122 may be defined to avoid one or more undesirable obstacles, such as a blood vessel 500, a previously utilized transcutaneous path 502, a nerve, or the like, as illustrated in FIG. 5. A variety of techniques, including various techniques for medical imaging, may be utilized to identify such undesirable obstacles as necessary.

Figure 2:
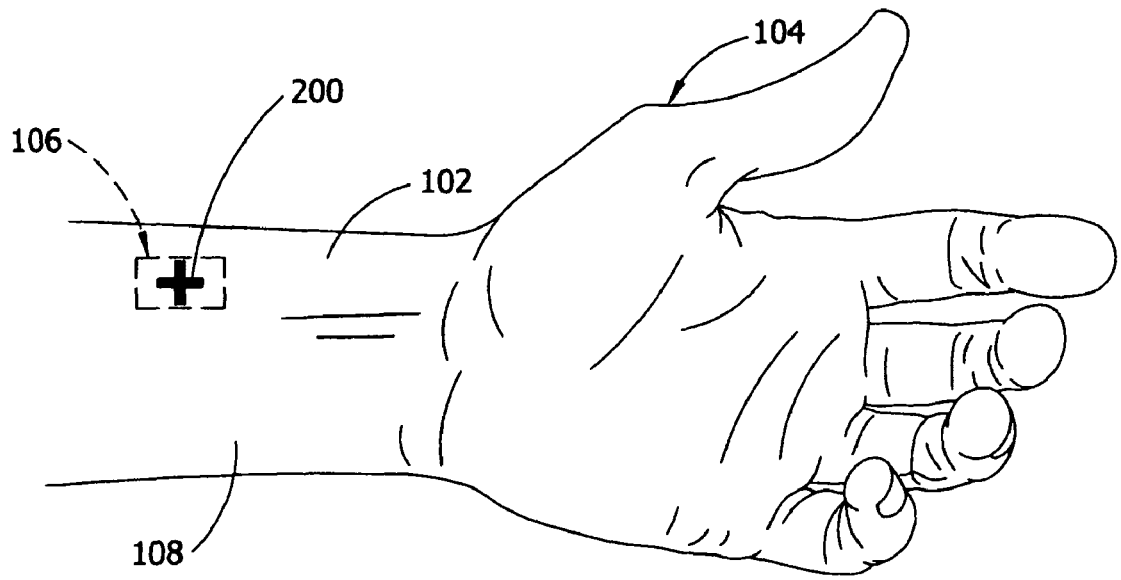
FIG. 2 is a schematic of a subject including a subcutaneous device.

In order to align the output port 114 of the first device 100 with the receiving port 116 of the subdermal second device 106, a fiducial may be located on the subject 104. For example, as illustrated in FIG. 2, a marking (e.g., a tattoo 200) may be placed on the subject 104. The tattoo 200 may be a temporary tattoo, a marking made with a permanent or semi-permanent ink, or another type of marking not easily removed (e.g., not removable with soap and water in one or two thorough washings). In an embodiment, the marking is selected to last for the duration of treatment or the lifetime of the subdermal second device 106. In other embodiments, the marking may be reapplied as necessary. In a still further embodiment, the subdermal second device 106 may be placed within the subject 104 at a predefined location selected for its known proximity to a preexisting fiducial, such as a tattoo, a piercing, a birthmark, or a variety of readily identifiable body features and locations.

Alternatively, a fiducial 124 may be placed on the subdermal second device 106. In an embodiment, the fiducial 124 may include a fluorescent marker. In another embodiment, the fiducial 124 may include a marker having an enhanced radio signature (e.g., a material for emitting or reflecting a radio signal). In a still further embodiment, the fiducial 124 may include a radio frequency identification tag. Alternatively, the fiducial 124 may include a radio opaque marker. The fiducial 124 may include a retroreflector (i.e., a device with enhanced optical reflection, making its surface appear brighter than it would otherwise be). Further, the fiducial 124 may include an ultrasonic marker. It will be appreciated, in light of the description provided herein, that the fiducial 124 may include a variety of location aids.

In certain embodiments, the subdermal second device 106 may transmit a signal 126 to the first device 100 for aligning the output port 114 of the first device 100 with the receiving port 116 of the subdermal second device 106. In an embodiment, the signal 126 may include an electrical current. In another embodiment, the signal 126 may include an electrical field. In a still further embodiment, the signal 126 may include a magnetic flux. Alternatively, the signal 126 may include an optical signal, e.g., from a Light Emitting Diode (LED). The signal 126 may include a Radio Frequency Identification (RFID). Further, the signal 126 may include an ultrasonic signal. It will be appreciated, in light of the description provided herein, that the signal 126 may be transmitted in a variety of formats.

Alternatively, the signal 126 generated by the subdermal second device 106 may be transmitted from the subdermal second device 106 to inform the first device 100 (or another interested party) of information regarding the material 112. Thus, the signal 126 may include information regarding a need for the material 112, a need for a quantity of the material 112, a need for a type of the material 112, or a quantity of the material 112 collected. The signal 126 may also indicate a ready condition for receiving the material 112 or provide feedback regarding whether the material 112 is received by the subdermal second device 106. Thus, the signal 126 may be utilized to stop transfer of the material 112 if the material is not received by the subdermal second device 106. Alternatively, the signal 126 may be utilized to compare an amount of the material 112 collected by the subdermal second device 106 to an amount of the material 112 transferred by the first device 100. Further, the signal 126 may be utilized to stop transfer of the material 112 when the subdermal second device 106 does not require more of the material (e.g., when the second reservoir 120 of the subdermal second device 106 is full). Further, the first device 100 may include a receiver 128 for receiving the signal 126 from the subdermal second device 106 and coordinating the transfer of the material 112 from the first device 100 to the subdermal second device 106. For example, the subdermal second device 106 may contain one or more sensors for detecting an amount of material contained in the second reservoir 120. When the material is at a desired level within the second reservoir 120, a sensor may cause a signal 126 to be sent by a signal generation and transmission mechanism, such as an ultrasonic transmitter, or the like. In this embodiment, receipt of the ultrasonic signal by the first device 100 may cause the first device 100 to stop transfer of the material 112.

In certain embodiments, either or both of the first device 100 and the subdermal second device 106 may include one or more reservoirs for storing material. For example, in embodiments illustrated in FIGS. 3 and 4, the first device 100 may include a third reservoir 300, and the subdermal second device 106 may include a fourth reservoir 302. The third reservoir 300 and the fourth reservoir 302 may be utilized for storing another material 304. The material 304 may be a second material different from the first material 112 (e.g., in a case where multiple materials are stored by the subdermal second device 106). Alternatively, the material 304 may be the same as the material 112 (e.g., in a case where multiple doses of the same material are stored by the subdermal second device 106).

Figure 3:
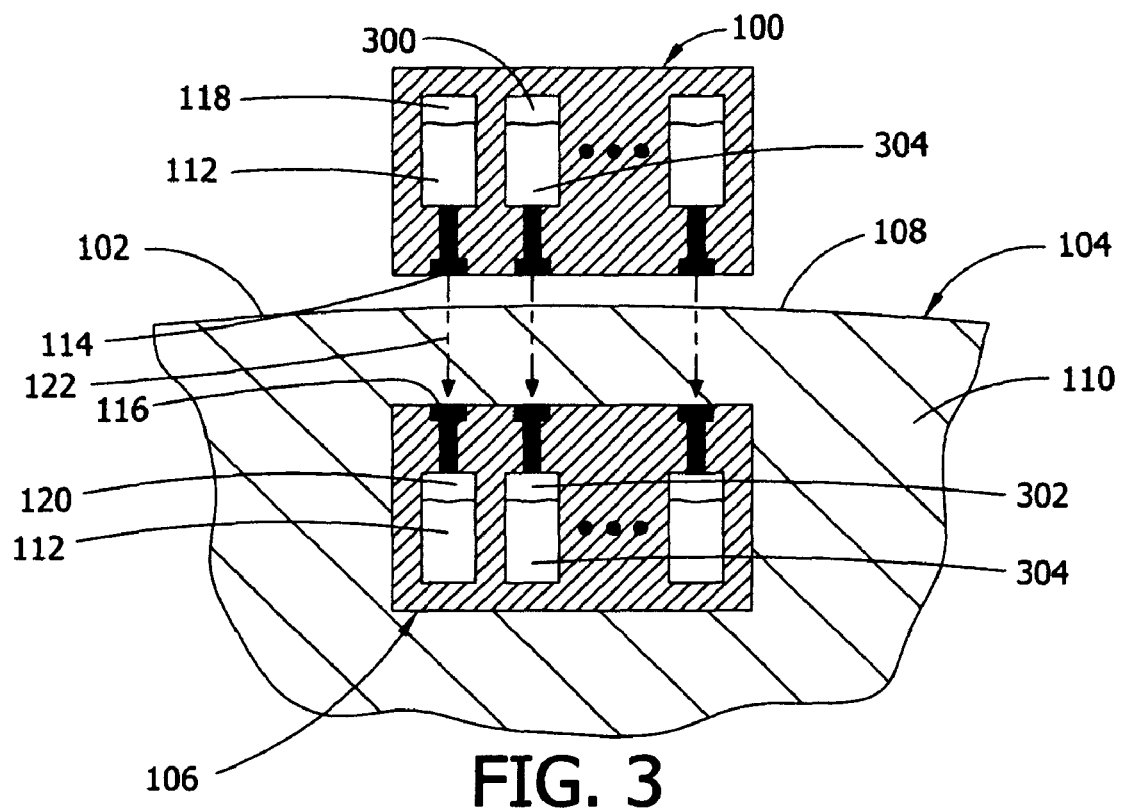
FIG. 3 is another schematic of a device for transferring material through a skin portion of a subject to a second subcutaneous device.
Figure 4:
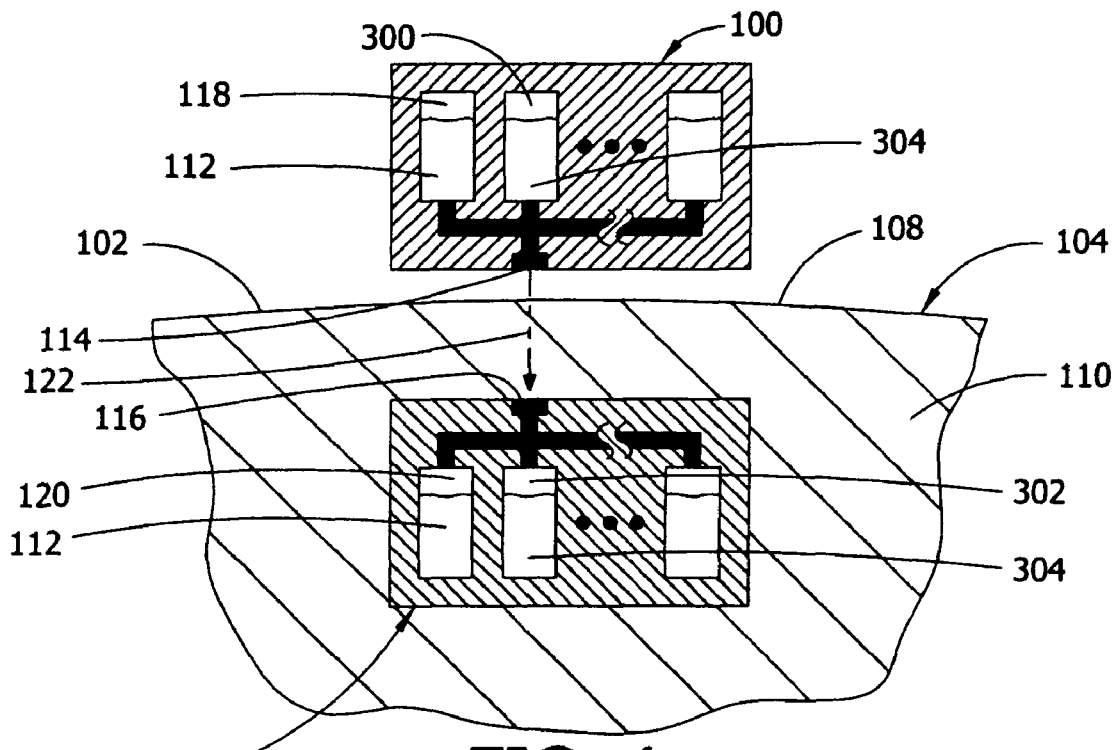
FIG. 4 is a further schematic of a device for transferring material through a skin portion of a subject to a second subcutaneous device.

It will be appreciated in light of the description provided herein, that the third reservoir 300 and the fourth reservoir 302 may be connected to separate output ports and receiving ports (as illustrated in FIG. 3) or connected to the same output ports and receiving ports as the first reservoir 118 and the second reservoir 120, respectively (as illustrated in FIG. 4). Further, in the embodiment illustrated in FIG. 3, the output port of the third reservoir 300 may be aligned with the receiving port of the fourth reservoir 302 (as previously described) for transporting the material 304 from the first device 100 to the subdermal second device 106. It is contemplated that the first device 100 and the subdermal second device 106 may each include more than two reservoirs for storing and receiving various materials, including three reservoirs, four reservoirs, and more than four reservoirs. Further, it will be appreciated, in light of the description provided herein, that the various reservoirs may be connected to various output ports and receiving ports. For example, in an embodiment illustrated in FIG. 5, the first reservoir 118 and the second reservoir 120 may be connected to a second output port 504 and a second receiving port 506.

Figure 6:
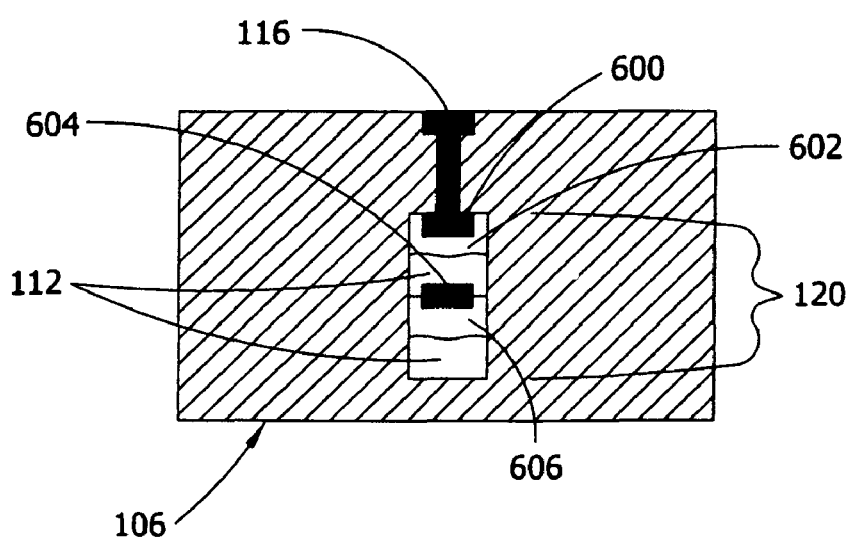
FIG. 6 is a schematic of a subcutaneous device for receiving material transferred through a skin portion of a subject.

In an embodiment illustrated in FIG. 6, the receiving port 116 of the subdermal second device 106 includes a first window 600 for providing access to an antechamber 602 of the second reservoir 120, and one or more second windows 604 for providing access to one or more inner chamber 606 of the second reservoir 120. The first window 600 or the one or more second windows 604 may be controllable. For example, the subdermal second device 106 may include one or more motors or other device(s) for controlling the windows 600, 604. It will be appreciated that the amount the windows are open may be controllable as well, such as the diameter/opening width to which the windows are opened.

In an embodiment, the subdermal second device 106 is powered by a power source outside the body of the subject 104. The first device 100 may include a power provider. The subdermal second device 106 may include a power receiver. The first device 100 may provide power to the subdermal second device 106 via the power provider and the power receiver. For example, the power provider may be connected to an AC power source and may provide power to the subdermal second device 106 via the power receiver utilizing at least one dermal layer of the subject 104 as a conductive medium.

In another embodiment, the subdermal second device 106 may include an energy storage mechanism. For example, the energy storage mechanism may include, but is not limited to, a lithium-ion battery, an alkaline battery, a lead acid battery, an absorbed glass mat battery, a thermal battery, a chloroaluminate battery, a nickel-zinc battery, a nickel cadmium battery, an aluminum battery, a lithium battery, or a nickel metal hydride battery. The energy storage mechanism may be charged by a power source outside the body of the subject 104. The first device 100 may include a power provider. The subdermal second device 106 may include a power receiver. The first device 100 may charge the energy storage mechanism via the power provider and the power receiver. For example, the power provider may be connected to an AC power source and may charge the energy storage mechanism via the power receiver utilizing mutual induction.

Figure 7:
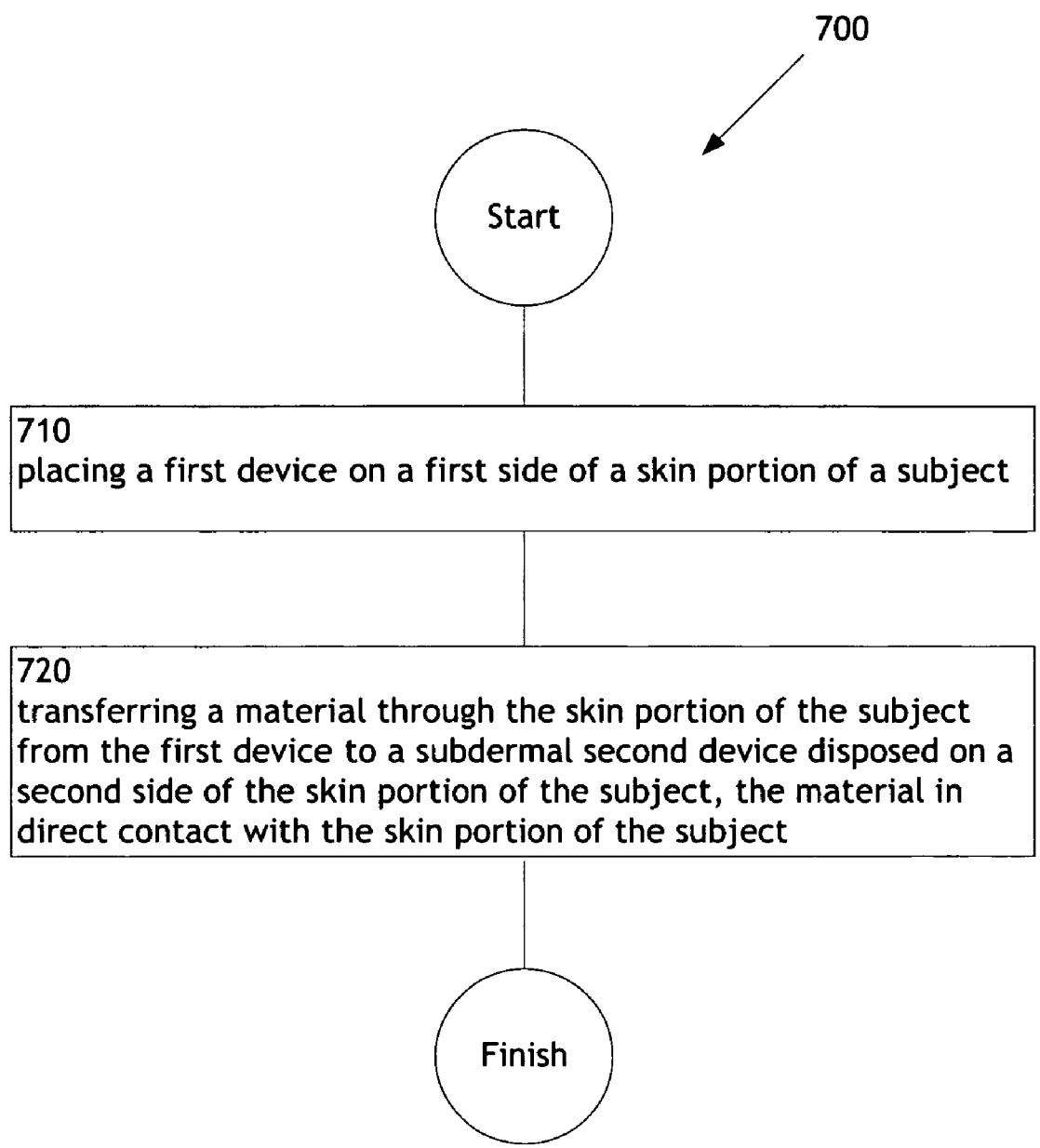
FIG. 7 illustrates an operational flow representing example operations related to transferring material through a skin portion a subject to a subcutaneous device.

FIG. 7 illustrates an operational flow 700 representing example operations related to transferring material through a skin portion 102 of a subject 104 to a subcutaneous/subdermal second device 106. In FIG. 7 and in following figures that include various examples of operational flows, discussion and explanation may be provided with respect to the above-described examples of FIGS. 1 through 6, or with respect to other examples and contexts. However, it will be understood, in light of the description provided herein, that the operational flows may be executed in a number of other environments and contexts, or in modified versions of FIGS. 1 through 6. Also, although the various operational flows are presented in the sequence(s) illustrated, it will be understood, in light of the description provided herein, that the various operations may be performed in other orders than those which are illustrated, or may be performed concurrently.

After a start operation, the operational flow 700 moves to a placing operation 710, where a first device may be placed on a first side of a skin portion of a subject. For example, as shown in FIGS. 1 through 6, the first device 100 may be placed on the first side 108 of the skin portion 102 of the subject 104.

Then, in a transferring operation 720, a material may be transferred through the skin portion of the subject from the first device to a subdermal second device disposed on a second side of the skin portion of the subject, the material in direct contact with the skin portion of the subject. For example, as shown in FIGS. 1 through 6, the material 112 may be transferred from the first device 100 to the subdermal second device 106 through the skin portion 102 of the subject 104, where the subdermal second device 106 is placed on the second side 110 of the skin portion 102 of the subject 104.

Figure 8:
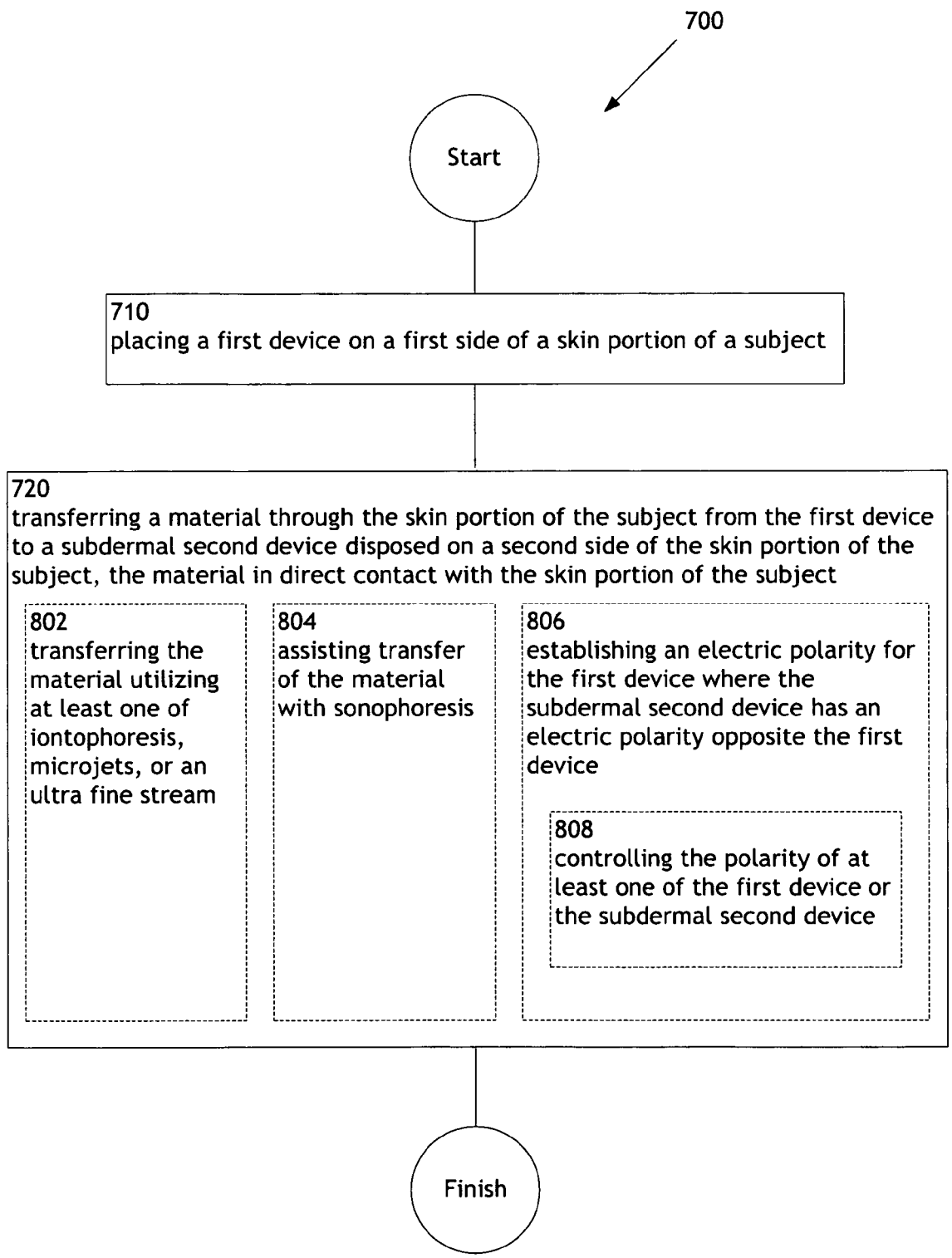
FIG. 8 illustrates an alternative embodiment of the operational flow of FIG. 7.

FIG. 8 illustrates alternative embodiments of the example operational flow 700 of FIG. 7. FIG. 8 illustrates embodiments where the transferring operation 720 may include at least one additional operation. Additional operations may include an operation 802, an operation 804, an operation 806, or an operation 808.

At the operation 802, the material may be transferred utilizing at least one of iontophoresis, microjets, or an ultra fine stream. For example, as shown in FIGS. 1 through 6, the output port 114 of the first device 100 may include one or more microjets for propelling the material 112 through the skin portion 102 of the subject 104 to the input port/receiving port 116 of the subdermal second device 106.

At the operation 804, transfer of the material may be assisted with sonophoresis. For example, as shown in FIGS. 1 through 6, the material 112 may be topically applied to the first side 108 of the skin portion 102 of the subject 104. The first device 100 or the subdermal second device 106 may then generate ultrasound waves, assisting in the migration of the material 112 through the skin portion 102 of the subject 104 to the receiving port 116 of the subdermal second device 106.

At the operation 806, an electric polarity may be established for the first device where the subdermal second device has an electric polarity opposite the first device. For example, as shown in FIGS. 1 through 6, a first electrical polarity may be established for the first device 100 in opposition to a second electrical polarity for the subdermal second device 106. Further, at the operation 808, the polarity of at least one of the first device or the subdermal second device may be controlled. For example, as shown in FIGS. 1 through 6, the polarity of the first device 100 may be controlled as needed to assist with the transfer of the material 112.

Figure 9:
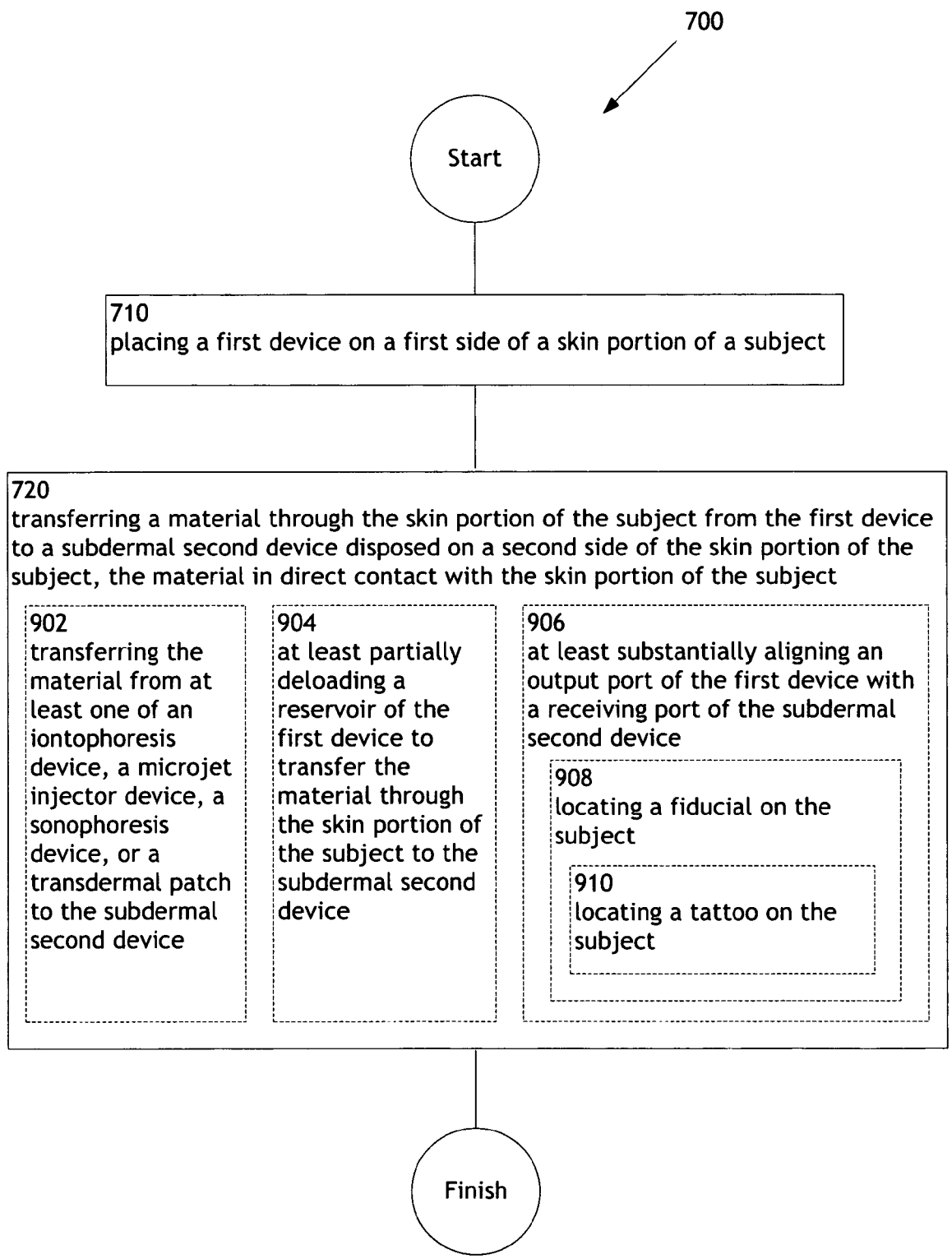
FIG. 9 illustrates an alternative embodiment of the operational flow of FIG. 7.

FIG. 9 illustrates alternative embodiments of the example operational flow 700 of FIG. 7. FIG. 9 illustrates embodiments where the transferring operation 720 may include at least one additional operation. Additional operations may include an operation 902, an operation 904, an operation 906, an operation 908, or an operation 910.

At the operation 902, the material may be transferred from at least one of an iontophoresis device, a microjet injector device, a sonophoresis device, or a transdermal patch to the subdermal second device. For example, as shown in FIGS. 1 through 6, the first device 100 may be a microjet injector device, in which the output port 114 includes one or more microjets for propelling the material 112 through the skin portion 102 of the subject 104 to the receiving port 116 of the subdermal second device 106.

At the operation 904, a reservoir of the first device may be at least partially deloaded to transfer the material through the skin portion of the subject to the subdermal second device. For example, as shown in FIGS. 1 through 6, the first reservoir 118 of the first device 100 may be at least partially deloaded to transfer the material 112 through the skin portion 102 of the subject 104 to the subdermal second device 106.

At the operation 906, an output port of the first device may be at least substantially aligned with a receiving port of the subdermal second device. For example, as shown in FIGS. 1 through 6, the output port 114 of the first device 100 may be aligned with the receiving port 116 of the subdermal second device 106. Further, at the operation 908, a fiducial may be located on the subject. For example, as shown in FIGS. 1 through 6, the subdermal second device 106 may be placed within the subject 104 at a predefined location selected for its known proximity to a fiducial (e.g., a tattoo, a piercing, or a birthmark). The fiducial may then be located to determine the position of the subdermal second device 106. Further, at the operation 910, a tattoo may be located on the subject. For example, as shown in FIGS. 1 through 6, the tattoo 200 may be located on the subject 104.

Figure 10:
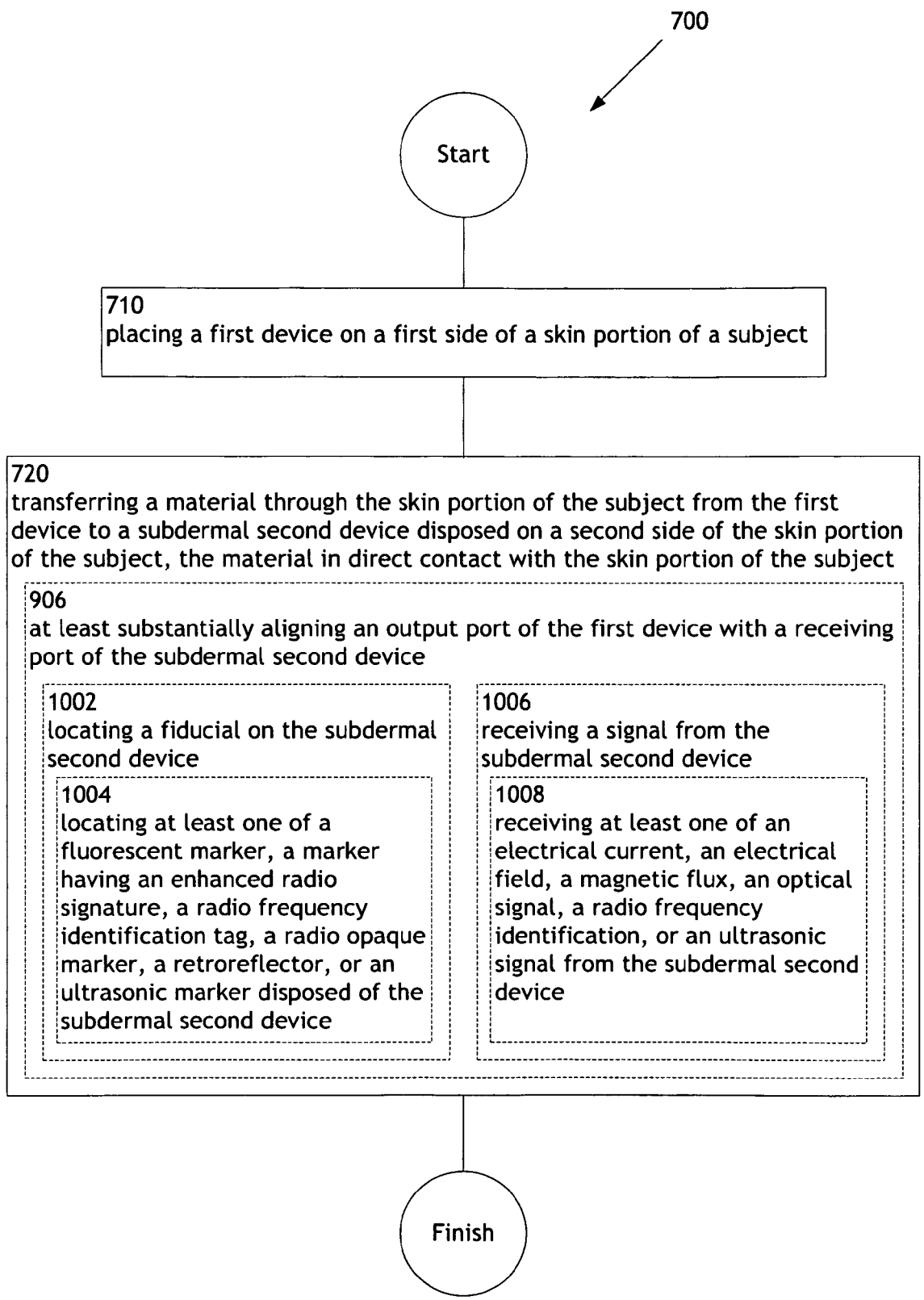
FIG. 10 illustrates an alternative embodiment of the operational flow of FIG. 7.

FIG. 10 illustrates alternative embodiments of the example operational flow 700 of FIG. 7. FIG. 10 illustrates embodiments where the transferring operation 720 may include at least one additional operation. Additional operations may include an operation 1002, an operation 1004, an operation 1006, or an operation 1008. At the operation 1002, a fiducial may be located on the subdermal second device. For example, as shown in FIGS. 1 through 6, the fiducial 124 may be located on the subdermal second device 106. Further, at the operation 1004, at least one of a fluorescent marker, a marker having an enhanced radio signature, a radio frequency identification tag, a radio opaque marker, a retroreflector, or an ultrasonic marker disposed of the subdermal second device may be located. For example, as shown in FIGS. 1 through 6, the fiducial 124 may include a radio frequency identification tag. Further, at the operation 1006, a signal from the subdermal second device may be received. For example, as shown in FIGS. 1 through 6 and continuing the previous example, the subdermal second device 106 may broadcast a radio frequency identification signal 126 to the first device 100 for aligning the output port 114 of the first device 100 with the receiving port 116 of the subdermal second device 106. Further, at the operation 1008, at least one of an electrical current, an electrical field, a magnetic flux, an optical signal, a radio frequency identification, or an ultrasonic signal may be received from the subdermal second device. For example, as shown in FIGS. 1 through 6 and continuing the previous example, the first device 100 receives the radio frequency identification signal 126 from the fiducial 124.

Figure 11:
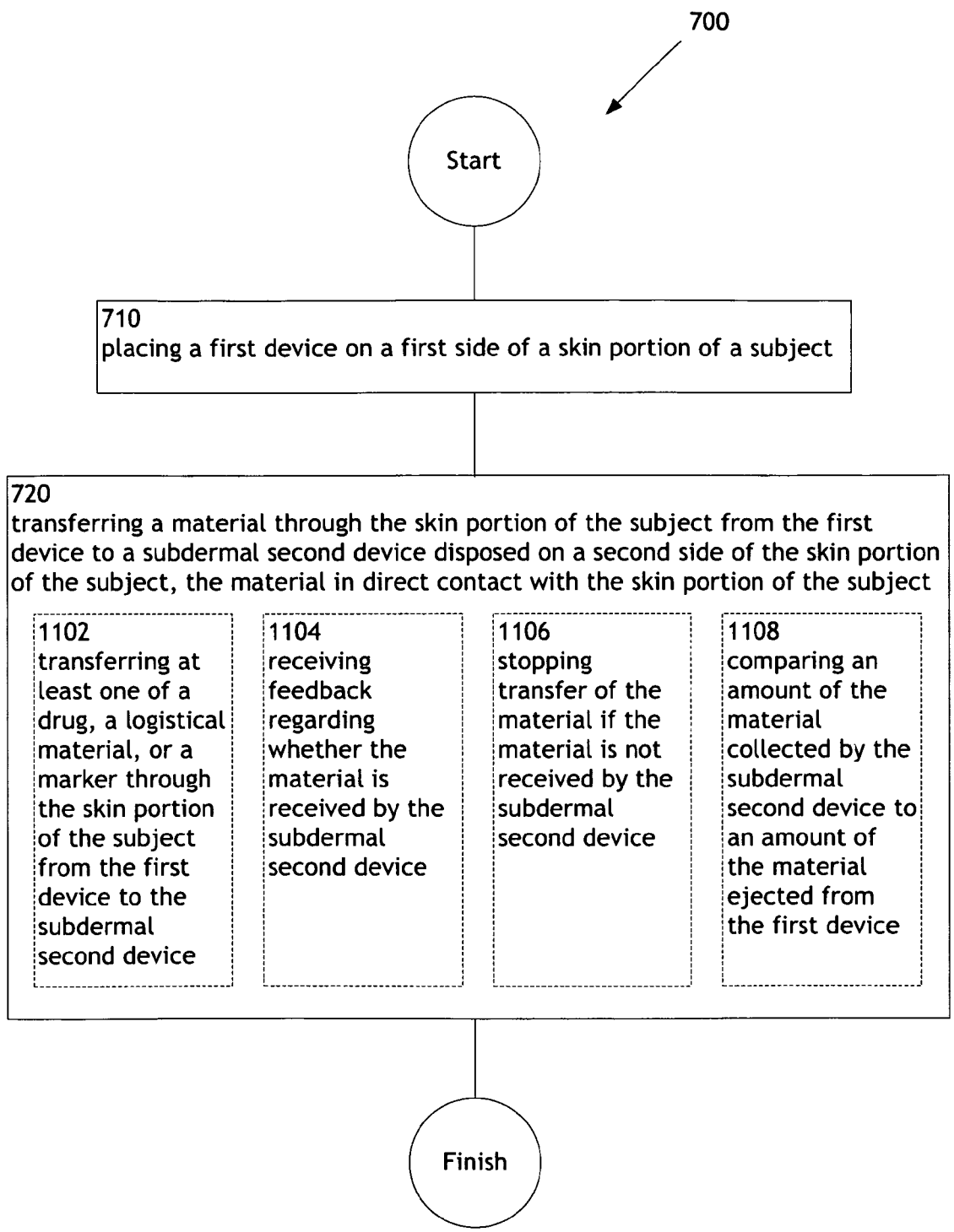
FIG. 11 illustrates an alternative embodiment of the operational flow of FIG. 7.

FIG. 11 illustrates alternative embodiments of the example operational flow 700 of FIG. 7. FIG. 11 illustrates embodiments where the transferring operation 720 may include at least one additional operation. Additional operations may include an operation 1102, an operation 1104, an operation 1106, or an operation 1108.

At the operation 1102, at least one of a drug, a logistical material, or a marker may be transferred through the skin portion of the subject from the first device to the subdermal second device. For example, as shown in FIGS. 1 through 6, the material 112 may include a marker/taggant for interacting with biological material, such as the subject's blood. Alternatively, the material 112 may include a drug for treating, preventing, or alleviating symptoms of an illness/disease. Further, the material 112 may include a logistical material (e.g., antibodies, nucleic acids, and the like).

At the operation 1104, feedback may be received regarding whether the material is received by the subdermal second device. For example, as shown in FIGS. 1 through 6, the signal 126 transmitted to the first device 100 (or another interested party) may provide feedback regarding whether the material 112 is received by the subdermal second device 106.

At the operation 1106, transfer of the material may be stopped if the material is not received by the subdermal second device. For example, as shown in FIGS. 1 through 6, the signal 126 may be utilized to stop transfer of the material 112 if the material is not received by the subdermal second device 106.

At the operation 1108, an amount of the material collected by the subdermal second device may be compared to an amount of the material ejected from the first device. For example, as shown in FIGS. 1 through 6, the signal 126 may be utilized to compare an amount of the material 112 collected by the subdermal second device 106 to an amount of the material 112 ejected from the first device 100.

Figure 12:
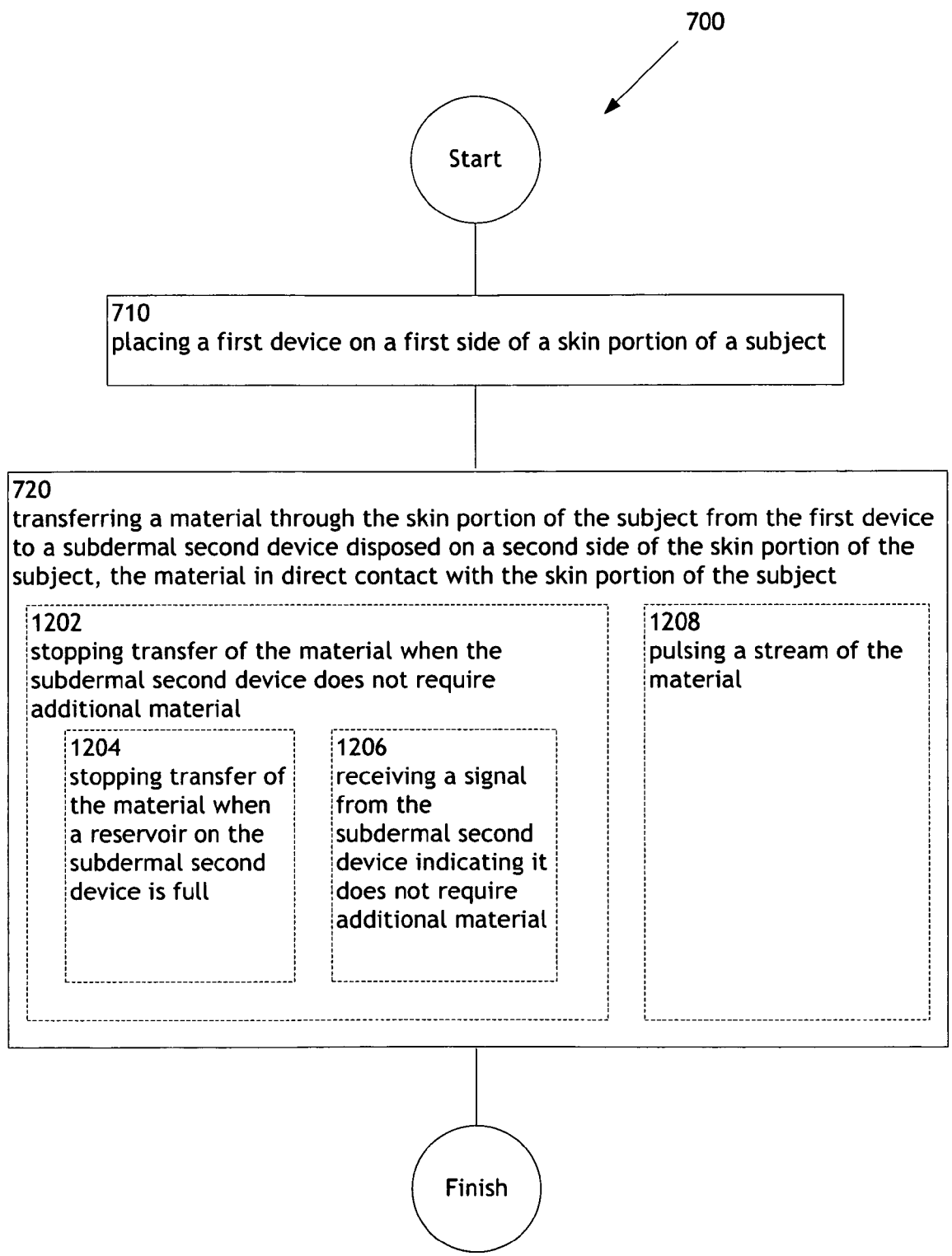
FIG. 12 illustrates an alternative embodiment of the operational flow of FIG. 7.

FIG. 12 illustrates alternative embodiments of the example operational flow 700 of FIG. 7. FIG. 12 illustrates embodiments where the transferring operation 720 may include at least one additional operation. Additional operations may include an operation 1202, an operation 1204, an operation 1206, or an operation 1208.

At the operation 1202, transfer of the material may be stopped when the subdermal second device does not require additional material. For example, as shown in FIGS. 1 through 6, the signal 126 may be utilized to stop transfer of the material 112 when the subdermal second device 106 does not require additional material 112. Further, at the operation 1204, transfer of the material may be stopped when a reservoir on the subdermal second device is full. For example, as shown in FIGS. 1 through 6 and continuing the previous example, the signal 126 may be utilized to stop transfer of the material 112 when the second reservoir 120 of the subdermal second device 106 is full. Further, at the operation 1206, a signal may be received from the subdermal second device indicating it does not require additional material. For example, as shown in FIGS. 1 through 6, the signal 126 may be received by the first device 100 and utilized to stop transfer of the material 112.

At the operation 1208, a stream of the material may be pulsed. For example, as shown in FIGS. 1 through 6, the output port 114 of the first device 100 may be utilized for pulsing a stream of the material 112 through the skin portion 102 of the subject 104 to the receiving port 116 of the subdermal second device 106. The first device 100 may force the material 112 through the skin portion 102 of the subject 104 as a liquid in a pulse in order to determine if the subdermal second device 106 is receiving the material 112 (e.g., prior to continuing to transfer the material 112 through the skin portion 102 of the subject 104). The first device 100 or the subdermal second device 106 may include one or more processors, memories, transmitters, and receivers for determining if the subdermal second device 106 is receiving the material 112.

Figure 13:
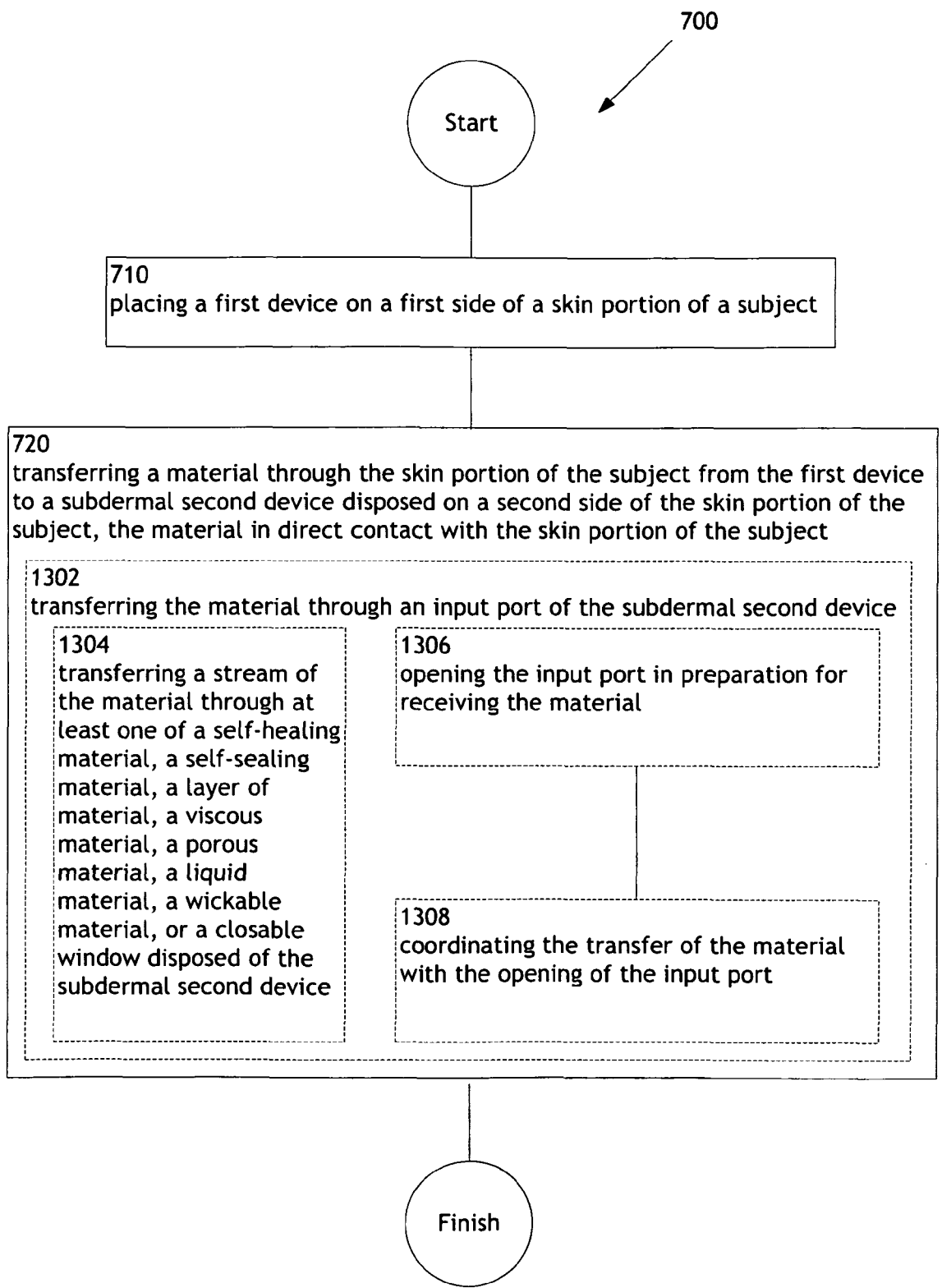
FIG. 13 illustrates an alternative embodiment of the operational flow of FIG. 7.

FIG. 13 illustrates alternative embodiments of the example operational flow 700 of FIG. 7. FIG. 13 illustrates embodiments where the transferring operation 720 may include at least one additional operation. Additional operations may include an operation 1302, an operation 1304, an operation 1306, or an operation 1308.

At the operation 1302, the material may be transferred through an input port of the subdermal second device. For example, as shown in FIGS. 1 through 6, the material 112 may be transferred through the receiving port 116 of the subdermal second device 106. Further, at the operation 1304, a stream of the material may be transferred through at least one of a self-healing material (e.g., an epoxy containing microcapsules filled with a liquid monomer or a supramolecular polymer), a self-sealing material (e.g., a hydrogel disposed of a porous substrate), a layer of material (e.g., a layer of plastic), a viscous material (e.g., a gel), a porous material (e.g., a material constructed utilizing a polymer or surfactant template), a second liquid material (e.g., a water-based solution), a wickable material (e.g., synthetic resins or fibers), or a closable window (e.g., an aperture covered by a leaf shutter) disposed of the subdermal second device. For example, as shown in FIGS. 1 through 6, a stream of the material 112 may be transferred through the receiving port 116 of the subdermal second device 106, where the receiving port 116 includes a self-healing material (e.g., a material capable of fully or partially restoring its integrity after being punctured by the stream of material 112). Further, the receiving port 116 may include a self-sealing material (e.g., a material capable of fully or partially resealing itself after being penetrated by the stream of material 112). Still further, the receiving port 116 may include a viscous material (e.g., a material that is viscous at the body temperature of the subject). Alternatively, the receiving port 116 may include a closable window, where the window is openable for receiving the material 112. It will be appreciated that the material 112 may be retained by one or more layers of material. Additionally, it will be appreciated that the material 112 may be retained by the subdermal second device 106 via surface tension in the case of a liquid material. Further, at the operation 1306, the input port may be opened in preparation for receiving the material. For example, as shown in FIGS. 1 through 6 and continuing a previous example, the receiving port 116 may include a closable window, where the window is openable for receiving the material 112. The window may be opened in preparation for receiving the material 112. Then, at the operation 1308, transfer of the material may be coordinated with the opening of the input port. For example, as shown in FIGS. 1 through 6 and continuing the previous example, the first device 100 or another external device, possibly connected to the first device 100, may transfer a signal to the subdermal second device 106 notifying the subdermal second device 106 to prepare for receiving the material 112. Subsequently, the subdermal second device 106 may open the closable window to receive the material 112.

Figure 14:
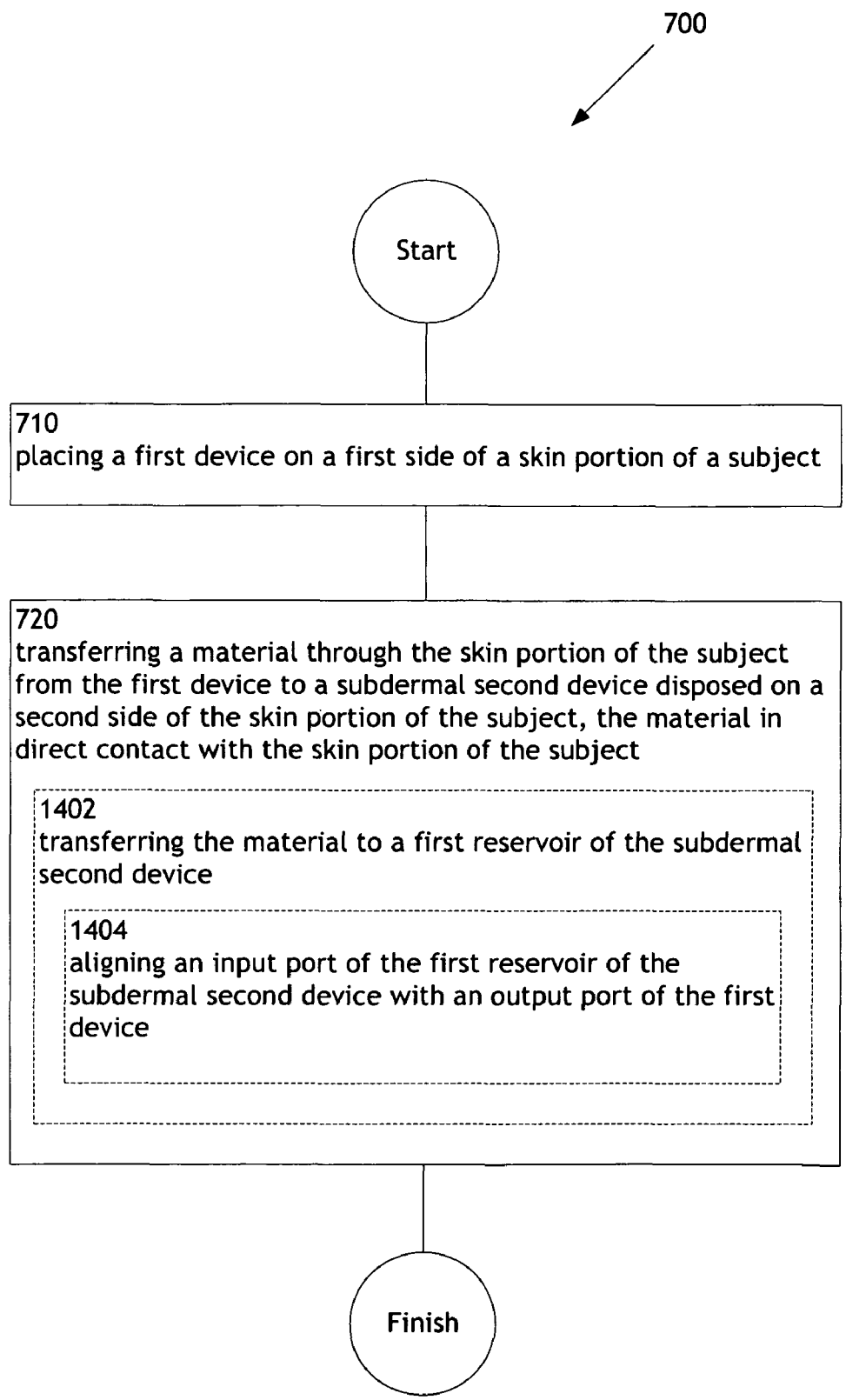
FIG. 14 illustrates an alternative embodiment of the operational flow of FIG. 7.

FIG. 14 illustrates alternative embodiments of the example operational flow 700 of FIG. 7. FIG. 14 illustrates embodiments where the transferring operation 720 may include at least one additional operation. Additional operations may include an operation 1402, or an operation 1404.

At the operation 1402, the material may be transferred to a first reservoir of the subdermal second device. For example, as shown in FIGS. 1 through 6, the material 112 may be transferred from the first device 100 to the second reservoir 120 of the subdermal second device 106. In one embodiment, the second reservoir 120 of the subdermal second device 106 is configured to rotate for retaining the material 112. For example, the rotation of the second reservoir 120 may bias the material 112 towards the walls of the second reservoir 120, retaining the material within the second reservoir 120 even when the receiving port 116 is in an opened orientation for receiving the material 112 (e.g., in the case of a closable window). Alternatively, the second reservoir 120 may include one or more walls constructed to have an attraction to the material 112 (e.g., the wall may be hydrophyllic in the case of a water-based material 112). Further, at the operation 1404, an input port of the first reservoir of the subdermal second device may be aligned with an output port of the first device. For example, as shown in FIGS. 1 through 6, this may be accomplished by at least substantially aligning the output port 114 of the first device 100 with the receiving port 116 of the subdermal second device 106.

Figure 15:
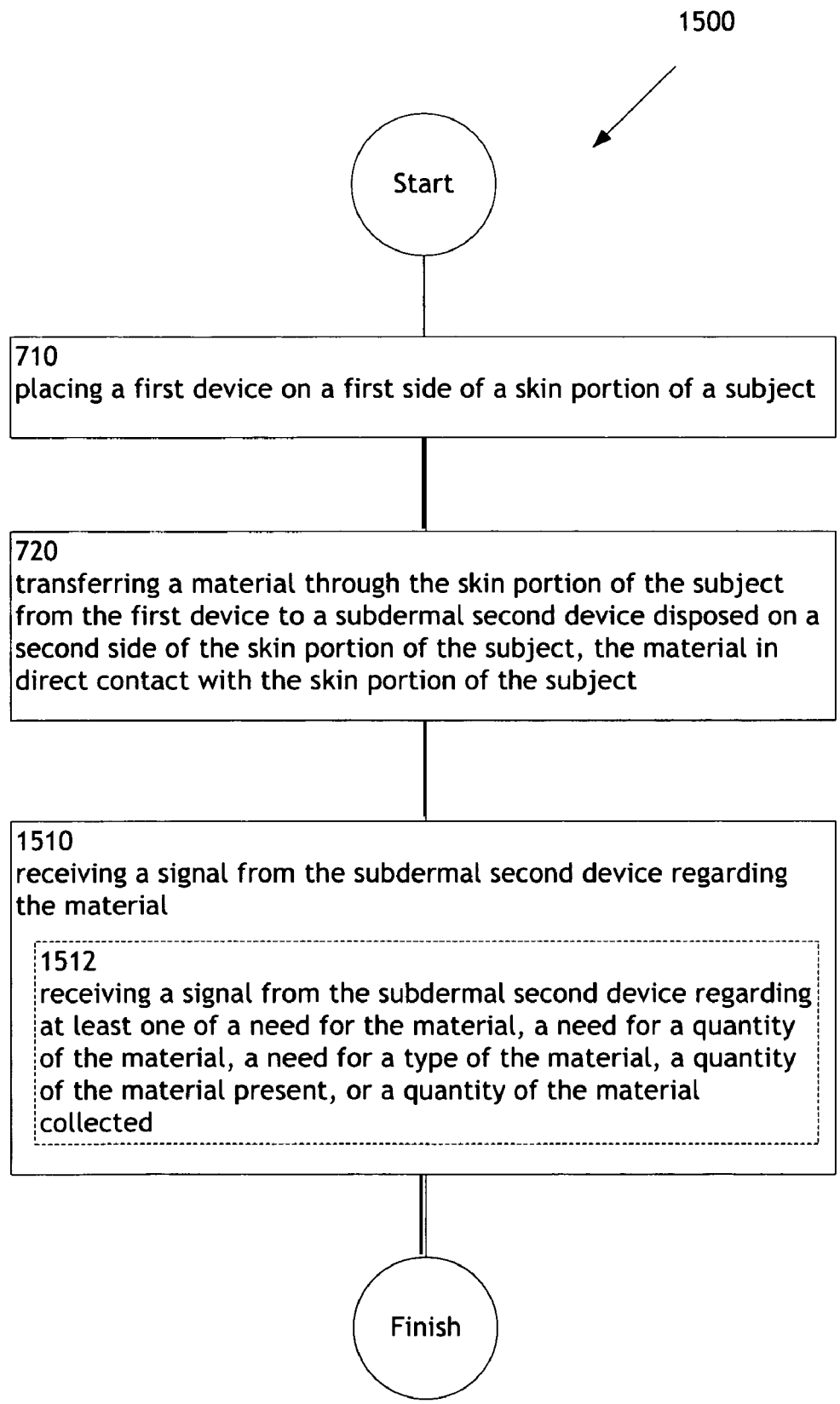
FIG. 15 illustrates an operational flow representing example operations related to transferring material through a skin portion a subject to a subcutaneous device.

FIG. 15 illustrates an operational flow 1500 representing example operations related to transferring material through a skin portion 102 of a subject 104 to a subcutaneous/subdermal second device 106. FIG. 15 illustrates an embodiment where the example operational flow 700 of FIG. 7 may include at least one additional operation. Additional operations may include an operation 1510, or an operation 1512.

After a start operation, a placing operation 710, and a transferring operation 720, the operational flow 1500 moves to a receiving operation 1510, where a signal from the subdermal second device may be received regarding the material. For example, as shown in FIGS. 1 through 6, the first device 100 (or another interested party, such as a monitoring station, a doctor's office, or the like) may receive a signal 126 regarding the material 112.

At the operation 1512, a signal may be received from the subdermal second device regarding at least one of a need for the material, a need for a quantity of the material, a need for a type of the material, a quantity of the material present, or a quantity of the material collected. For example, as shown in FIGS. 1 through 6 and continuing the previous example, the signal 126 received by the first device 100 may include information regarding a need for the material 112 by the subdermal second device 106.

Figure 16:
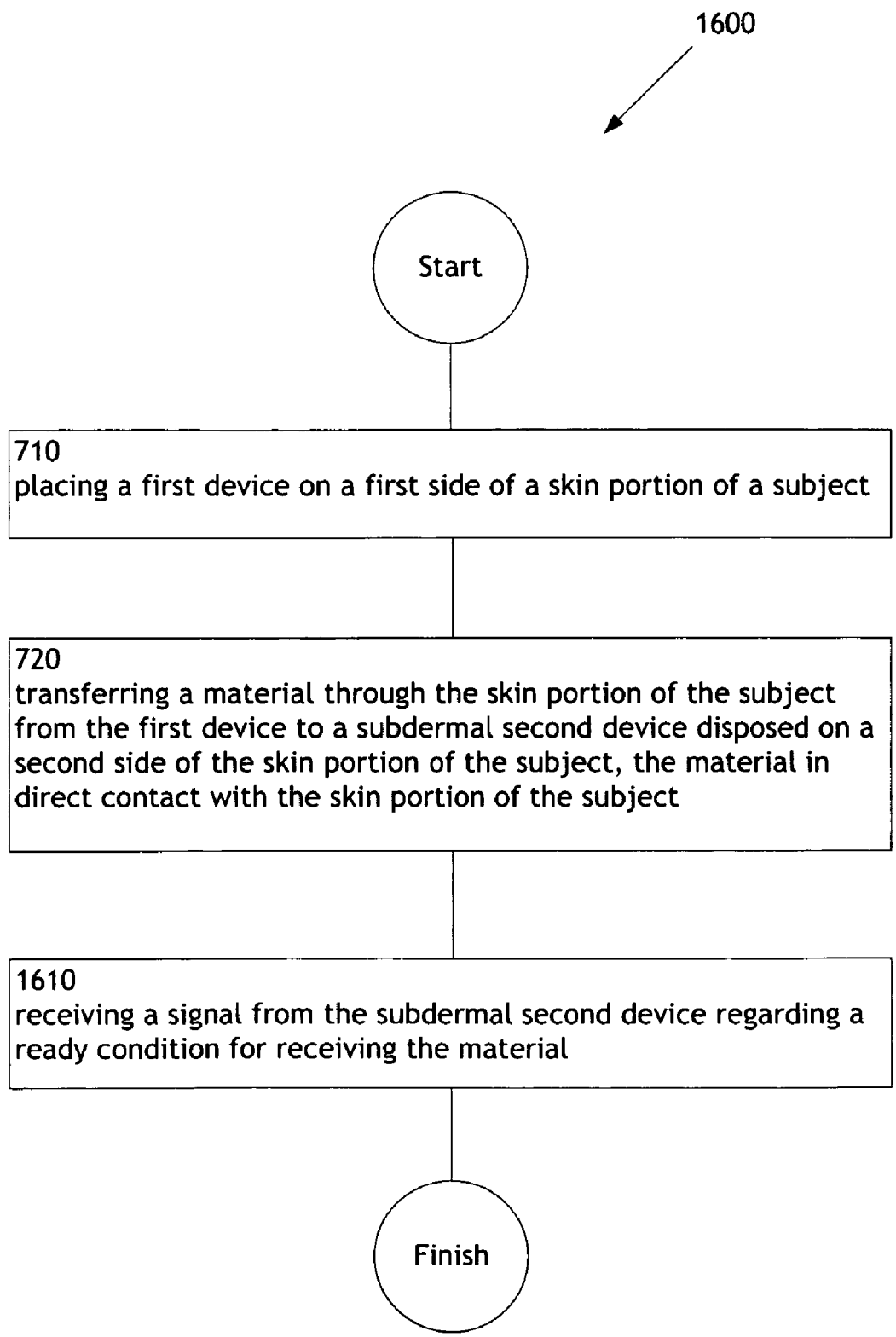
FIG. 16 illustrates an operational flow representing example operations related to transferring material through a skin portion a subject to a subcutaneous device.

FIG. 16 illustrates an operational flow 1600 representing example operations related to transferring material through a skin portion 102 of a subject 104 to a subcutaneous/subdermal second device 106. FIG. 16 illustrates an example embodiment where the example operational flow 700 of FIG. 7 may include at least one additional operation. Additional operations may include an operation 1610.

After a start operation, a placing operation 710, and a transferring operation 720, the operational flow 1600 moves to a receiving operation 1610, where a signal from the subdermal second device may be received regarding a ready condition for receiving the material. For example, as shown in FIGS. 1 through 6, the signal 126 may indicate a ready condition for receiving the material 112. In certain embodiments, a ready condition may include information regarding a port/pre-port that has been opened. For example, the signal 126 may indicate that a first window 600 for providing access to an antechamber 602 of the second reservoir 120 of the subdermal second device 106 has opened. Alternatively, the signal 126 may indicate that a second window 604 for providing access to an inner chamber 606 of the second reservoir 120 of the subdermal second device 106 has opened.

Figure 17:
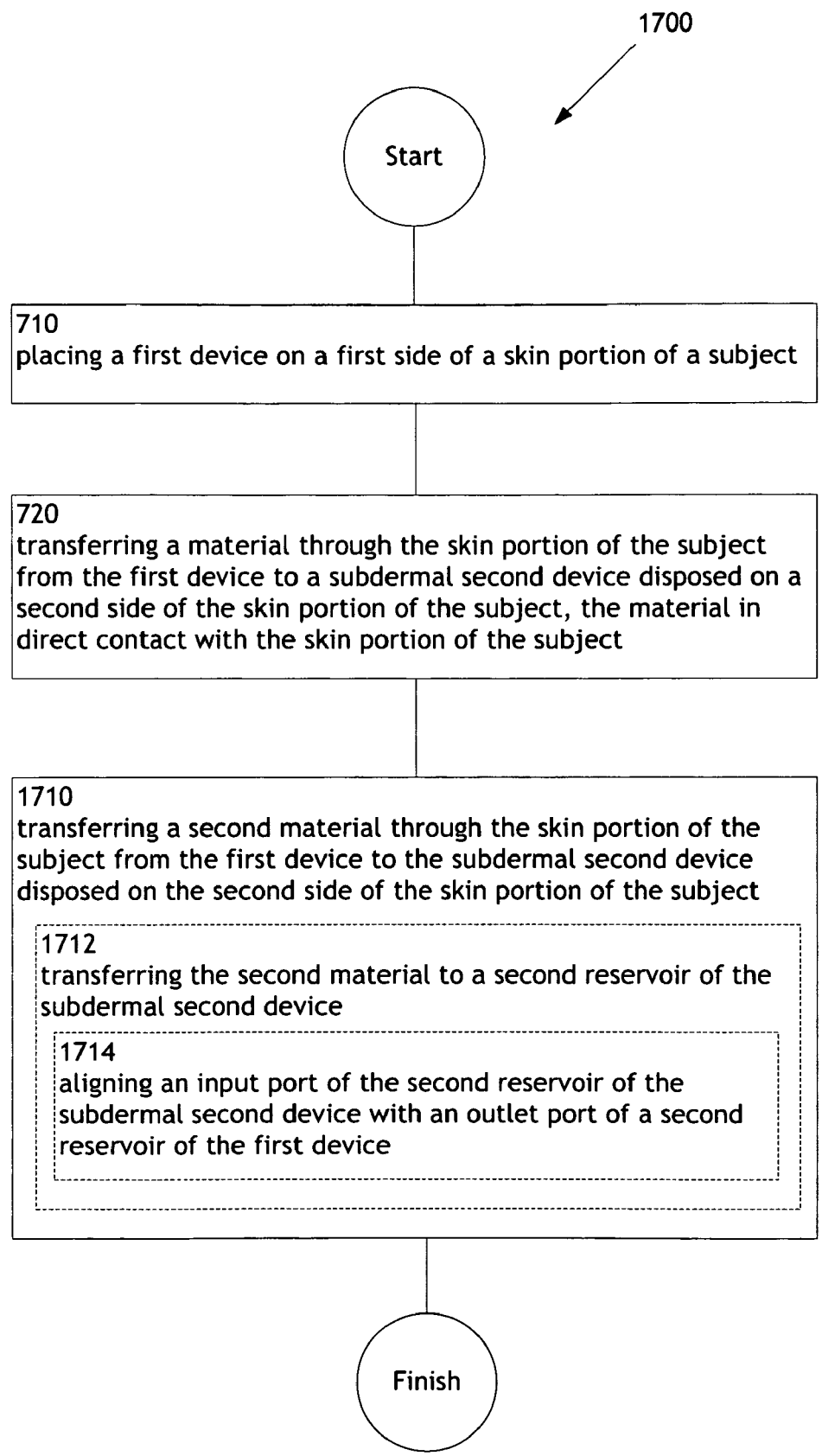
FIG. 17 illustrates an operational flow representing example operations related to transferring material through a skin portion a subject to a subcutaneous device.

FIG. 17 illustrates an operational flow 1700 representing example operations related to transferring material through a skin portion 102 of a subject 104 to a subcutaneous/subdermal second device 106. FIG. 17 illustrates an embodiment where the example operational flow 700 of FIG. 7 may include at least one additional operation. Additional operations may include an operation 1710, an operation 1712, or an operation 1714.

After a start operation, a placing operation 710, and a transferring operation 720, the operational flow 1700 moves to a second transferring operation 1710, where a second material may be transferred through the skin portion of the subject from the first device to the subdermal second device disposed on the second side of the skin portion of the subject. For example, as shown in FIGS. 1 through 6, the second material 304 may be transferred through the skin portion 102 of the subject 104 from the first device 100 to the subdermal second device 106.

At the operation 1712, the second material may be transferred to a second reservoir of the subdermal second device. For example, as shown in FIGS. 1 through 6 and continuing the previous example, the second material 304 may be transferred from the third reservoir 300 of the first device 100 to the fourth reservoir 302 of the subdermal second device 106. Further, at the operation 1714, an input port of the second reservoir of the subdermal second device may be aligned with an outlet port of a second reservoir of the first device. For example, as shown in FIGS. 1 through 6 and continuing the previous example, the output port of the third reservoir 300 may be aligned with the receiving port of the fourth reservoir 302 in preparation for receiving the second material 304.

Figure 18:
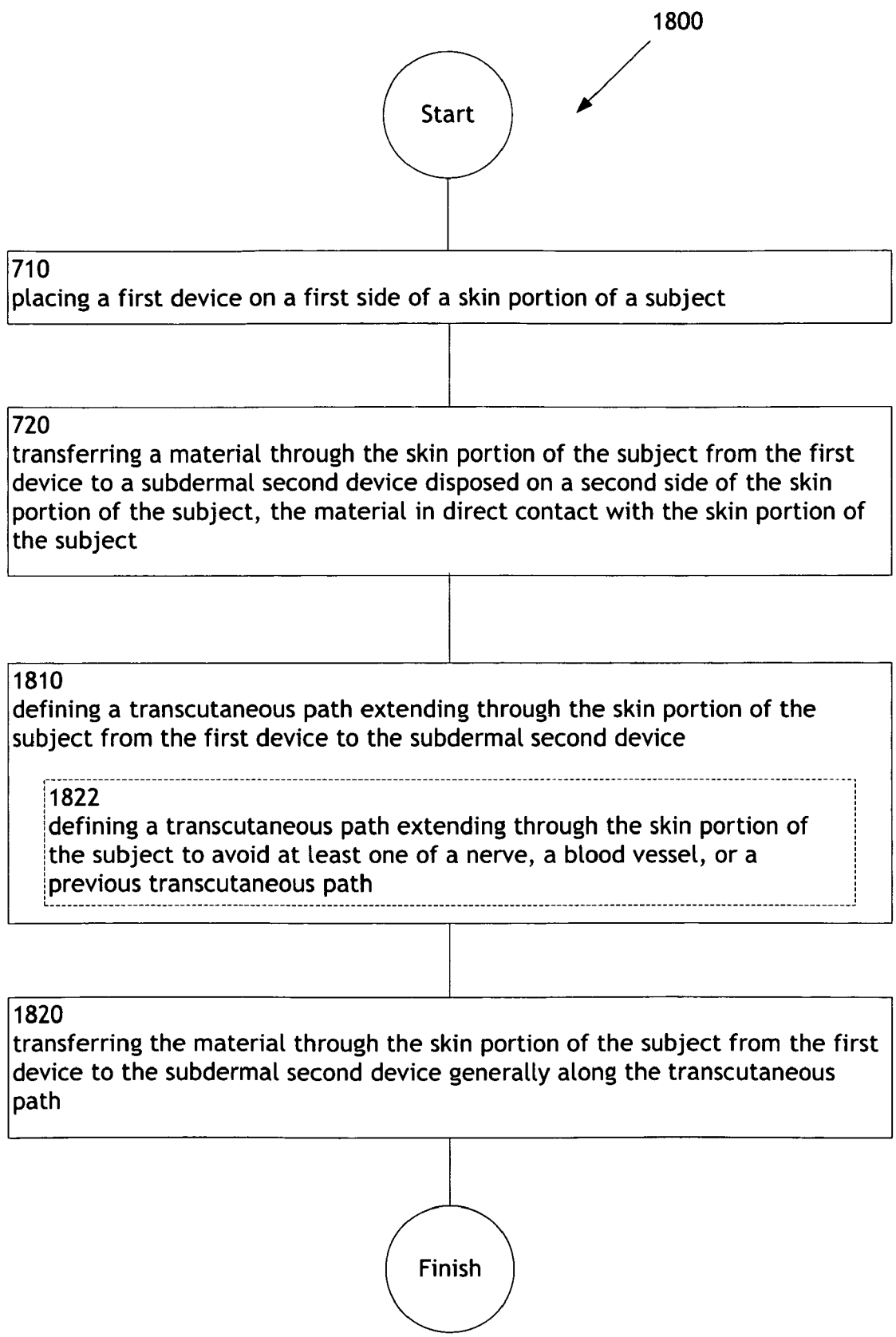
FIG. 18 illustrates an operational flow representing example operations related to transferring material through a skin portion a subject to a subcutaneous device.

FIG. 18 illustrates an operational flow 1800 representing example operations related to transferring material through a skin portion 102 of a subject 104 to a subcutaneous/subdermal second device 106. FIG. 18 illustrates an embodiment where the example operational flow 700 of FIG. 7 may include at least one additional operation. Additional operations may include an operation 1810, an operation 1820, or an operation 1822.

After a start operation, a placing operation 710, and a transferring operation 720, the operational flow 1800 moves to a defining operation 1810, where a transcutaneous path extending through the skin portion of the subject from the first device to the subdermal second device may be defined. For example, as shown in FIGS. 1 through 6, a transcutaneous path 122 extending through the skin portion 102 of the subject 104 from the first device 100 to the subdermal second device 106 may be defined.

Then, in a transferring operation 1820, the material may be transferred through the skin portion of the subject from the first device to the subdermal second device generally along the transcutaneous path. For example, as shown in FIGS. 1 through 6, the material 112 may be transferred through the skin portion 102 of the subject 104 generally along the transcutaneous path 122.

At the operation 1822, a transcutaneous path extending through the skin portion of the subject may be defined to avoid at least one of a nerve, a blood vessel, or a previous transcutaneous path. For example, as shown in FIGS. 1 through 6, the transcutaneous path 122 may be defined to avoid a blood vessel 500.

Figure 19:
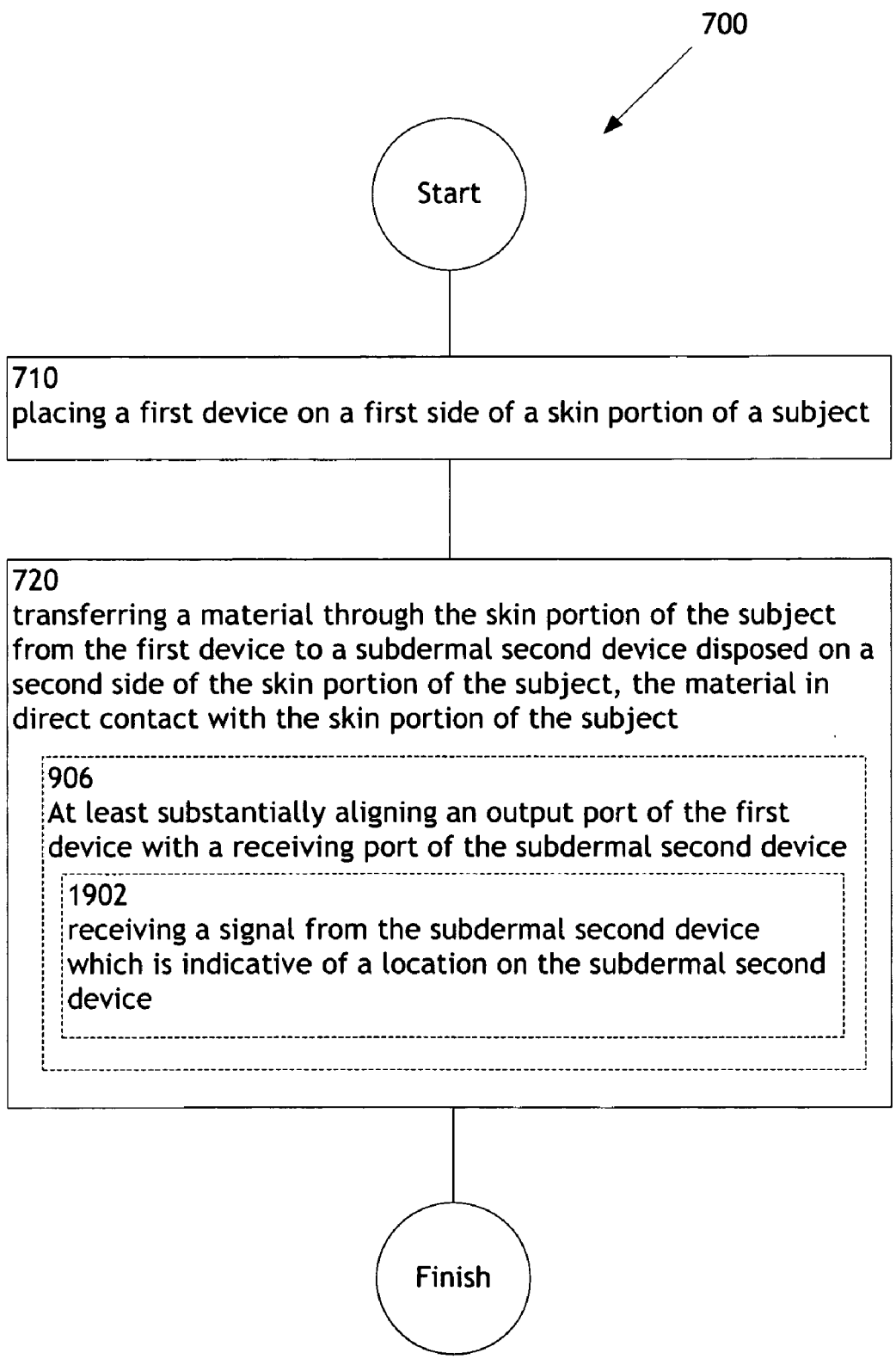
FIG. 19 illustrates an alternative embodiment of the operational flow of FIG. 7.

FIG. 19 illustrates alternative embodiments of the example operational flow 700 of FIG. 7. FIG. 19 illustrates embodiments where the transferring operation 720 may include at least one additional operation. Additional operations may include an operation 1902. At the operation 1902, a signal from the subdermal second device which is indicative of a location on the subdermal second device may be received. For example, as shown in FIGS. 1 through 6, the subdermal second device 106 may transmit a signal to the first device 100 indicating a location on the subdermal second device 106, such as the location of the receiving port 116. The location of the receiving port 116 may be transmitted as a set of coordinates, a vector oriented from a known position on the subdermal second device 106, or in another format as desired.

Figure 20:
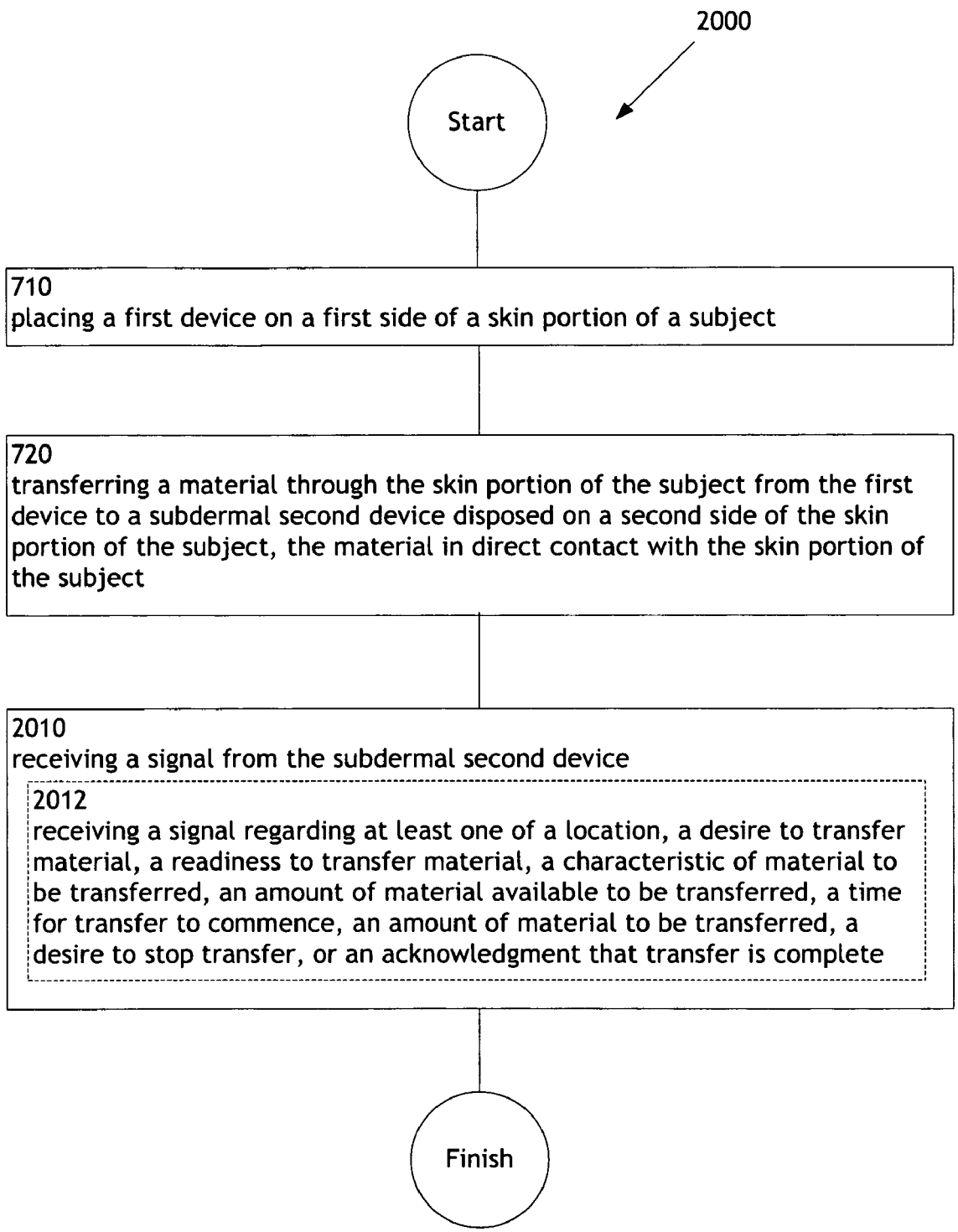
FIG. 20 illustrates an operational flow representing example operations related to transferring material through a skin portion a subject to a subcutaneous device.

FIG. 20 illustrates an operational flow 2000 representing example operations related to transferring material through a skin portion 102 of a subject 104 to a subcutaneous/subdermal second device 106. FIG. 20 illustrates an embodiment where the example operational flow 700 of FIG. 7 may include at least one additional operation. Additional operations may include an operation 2010, or an operation 2012.

After a start operation, a placing operation 710, and a transferring operation 720, the operational flow 2000 moves to a receiving operation 2010, where a signal from the subdermal second device may be received. For example, as shown in FIGS. 1 through 6, the first device 100 may receive a signal 126 from the subdermal second device 106.

At the operation 2012, a signal may be received regarding at least one of a location, a desire to transfer material, a readiness to transfer material, a characteristic of material to be transferred, an amount of material available to be transferred, a time for transfer to commence, an amount of material to be transferred, a desire to stop transfer, or an acknowledgement that transfer is complete. For example, as shown in FIGS. 1 through 6, the first device 100 may receive a signal 126 from the subdermal second device 106 regarding a location for a material, such as the location of a receiving port 116. Alternatively, the signal 126 may indicate a desire to transfer material (e.g., a signal indicating the subdermal second device 106 is in need of additional material), a readiness to transfer material (e.g., at a time when the subdermal second device 106 is ready to receive material), a characteristic of material to be transferred (e.g., a desired concentration of a drug), an amount of material available to be transferred (e.g., an amount of material present in the first device 100), a time for transfer to commence (e.g., for scheduling a transfer of material), an amount of material to be transferred (e.g., a specific number of grams of a material), a desire to stop transfer (e.g., a signal indicating the subdermal second device 106 is full), or an acknowledgement that transfer is complete (e.g., a signal indicating the subdermal second device 106 has as much of a material as it needs).

Figure 21:
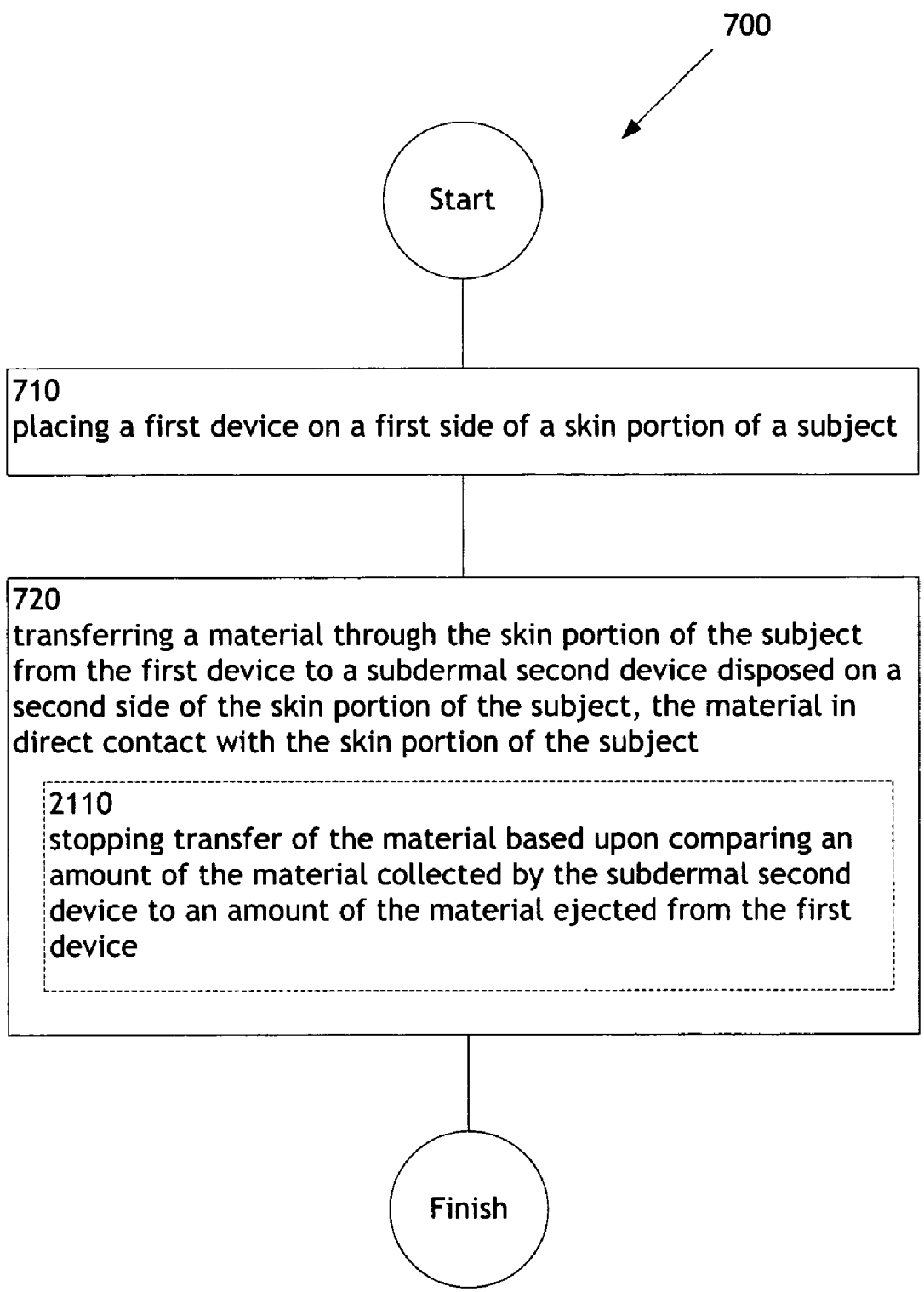
FIG. 21 illustrates an alternative embodiment of the operational flow of FIG. 7.

FIG. 21 illustrates alternative embodiments of the example operational flow 700 of FIG. 7. FIG. 21 illustrates embodiments where the transferring operation 720 may include at least one additional operation. Additional operations may include an operation 2110.

At the operation 2110, transfer of the material may be stopped based upon comparing an amount of the material collected by the subdermal second device to an amount of the material ejected from the first device. For example, as shown in FIGS. 1 through 6, the subdermal second device 106 may signal 126 the first device 100 regarding an amount of material received. In a case where the amount of material received is different from an amount of material sent/ejected from the first device 100, a determination may be made regarding the efficacy of the transfer. In a case where the material transferred from the first device 100 to the subdermal second device 106 is less than the amount of material received by the subdermal second device 106, the transfer may be stopped. In this instance, the first device 100 and the subdermal second device 106 may need to be realigned for a more effective transfer of material. Alternatively, a determination may be made that the material is being diverted by an obstacle, absorbed by the subject, or the like.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electromechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electromechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electromechanical systems include but are not limited to a variety of consumer electronics systems, medical devices, as well as other systems such as motorized transport systems, factory automation systems, security systems, and/or communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A system, comprising:
   a first device including:
      a first reservoir configured for placement externally to a skin portion of a subject, the first reservoir configured to store a liquid material;
      an output port operably connected to the first reservoir to transfer a material through, and in direct contact with, the skin portion of the subject;
   a second device including:
      a second reservoir configured for placement subdermally to the skin portion of the subject;
      an input port operably connected to the second reservoir, the input port configured for placement subdermally to the skin portion to receive the liquid material transferred through, and in direct contact with, the skin portion of the subject from the output port of the first device placed externally to the skin portion of the subject; and
      a fiducial, the fiducial positioned to align the output port of the first device with the input port of the second device for transfer of the liquid material from the first reservoir to the second reservoir.

2. The system of claim 1, wherein the input port comprises:
   at least one of the self-healing material, a self-sealing material, a layer of material, a viscous material, a porous material, a second liquid material, a wickable material, or a closable window.

3. The system of claim 1, wherein the input port comprises:
   a first window for providing access to an antechamber of the second reservoir; and
   one or more second windows for providing access to one or more inner chambers of the second reservoir.

4. The system of claim 1, wherein at least one of the first window or the one or more second windows is controllable.

5. The system of claim 1, wherein the second device further includes:
   a second port for receiving material transferred through the skin portion of the subject.

6. The system of claim 5, wherein the second port is operably connected to the second reservoir for receiving the liquid material transferred through the skin portion of the subject from the first device.

7. The system of claim 5, wherein the second port is operably connected to a third reservoir of the second device for receiving a second liquid material transferred through the skin portion of the subject.

8. The system of claim 1, wherein at least a portion of the second reservoir is configured to rotate to assist in retaining the liquid material.

9. The system of claim 1, wherein the second reservoir comprises:
   at least a portion of one wall constructed to have an attraction to the liquid material.

10. The system of claim 1, wherein the second reservoir comprises:
    at least a portion of one wall constructed to have a disattraction to the liquid material.

11. The system of claim 1, wherein the fiducial comprises:
    at least one of a fluorescent marker, a marker having an enhanced radio signature, a radio frequency identification tag, a radio opaque marker, a retroreflector, or an ultrasonic marker.

12. The system of claim 1, wherein the second device further includes:
    a transmitter for transmitting a signal to the first device.

13. The system of claim 12, wherein the signal comprises:
    at least one of an electrical current, an electrical field, a magnetic flux, an optical signal, a radio frequency identification, or an ultrasonic signal.

14. The system of claim 12, wherein the signal comprises:
    a signal regarding at least one of a need for the liquid material, a need for a quantity of the liquid material, a need for a type of the liquid material, a quantity of the liquid material collected, a location, cessation of a need for the liquid material, or a ready condition for receiving the liquid material.

15. The system of claim 1, wherein the second device further includes:
    a receiver for receiving a signal from the first device.

16. The system of claim 15, wherein the signal comprises:
    a signal regarding at least one of a location, a desire to transfer material, a readiness to transfer material, a characteristic of the liquid material to be transferred, an amount of material available to be transferred, a time for transfer to commence, an amount of material to be transferred, a desire to stop transfer, or an acknowledgement that transfer is complete.

17. The system of claim 4, further including:
    a motor to control at least one of the first window or the one or more second windows.

* * * * *